(12) United States Patent
Chang

(10) Patent No.: US 9,173,923 B2
(45) Date of Patent: Nov. 3, 2015

(54) MODULATING INNATE IMMUNE CELL ACTIVITY BY LUNASIN AND SELECTED CYTOKINES

(75) Inventor: Hua-Chen Chang, Indianapolis, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 14/123,202

(22) PCT Filed: May 31, 2012

(86) PCT No.: PCT/US2012/040144
§ 371 (c)(1),
(2), (4) Date: Nov. 30, 2013

(87) PCT Pub. No.: WO2012/166875
PCT Pub. Date: Dec. 6, 2012

(65) Prior Publication Data

US 2014/0099282 A1    Apr. 10, 2014

Related U.S. Application Data

(60) Provisional application No. 61/491,450, filed on May 31, 2011.

(51) Int. Cl.
*A61K 38/21* (2006.01)
*A61K 38/20* (2006.01)
*A61K 38/16* (2006.01)

(52) U.S. Cl.
CPC ........... *A61K 38/2086* (2013.01); *A61K 38/168* (2013.01); *A61K 38/2006* (2013.01); *A61K 38/208* (2013.01); *A61K 38/2013* (2013.01); *A61K 38/212* (2013.01)

(58) Field of Classification Search
None
See application file for complete search history.

(56) References Cited

U.S. PATENT DOCUMENTS

2010/0092497 A1* 4/2010 Kanwar et al. ............. 424/184.1

* cited by examiner

*Primary Examiner* — Brian J Gangle
*Assistant Examiner* — Andrea McCollum
(74) *Attorney, Agent, or Firm* — Faegre Baker Daniels LLP

(57) ABSTRACT

This disclosure provides compositions and methods for enhancing innate immune system activities and responses by combining lunasin with at least one cytokine. The compositions synergistically enhance the effect of these selected cytokine(s), including but not limited to, activating Natural Killer (NK) cells, augmenting NK's cytotoxicity against viruses and tumors, regulating NK mediated anti-allergic inflammation, producing potent NK cells for cellular therapy using adoptive transfer. and facilitating dendritic cells antigen presentation.

13 Claims, 25 Drawing Sheets

Dose-dependent effects of lunasin in combination with single or both IL-12 and IL-2

Synergistic effects of lunasin and IL-2 on IFNγ production by NK cells with acquired Stat4 deficiency following chemotherapy in a syngenic tumor mouse model

Combination of lunasin and both cytokines rescues IFNγ production by NK cells from NHL patients post-transplant with acquired STAT4 deficiency

Lunasin augments cytotoxicity by cytokine-activated NK cells in a xenograft model of human B-lymphoma

Lunasin augments NK-mediated cytotoxicity in human lung cancer cell lines

Effects of lunasin on IFNγ production by plasmacytoid dendritic cells (pDCs)

Effects of lunasin on gene expression by pDC

Effects of lunasin on gene expression by conventional DC (cDC)

Effects of lunasin on IFNγ production by mouse DCs and NK cells

Effects of lunasin on IFNγ production by mouse macrophages

Lunasin-treated mice have reduced allergic inflammation:
Lower cell counts in the bronchoalveolar lavage (BAL) fluid (A) and (B)
Reduced production of IL-4 (C)

Ctrl: low LPS sensitization, OVA challenge
LS: Low LPS sensitization with lunasin, OVA challenge
LC: Low LPS sensitization, OVA challenge with lunasin

SEQUENCE LISTING

```
<160> NUMBER OF SEQ ID NOS: 1

<210> SEQ ID NO 1
<211> LENGTH: 43
<212> TYPE: PRT
<213> ORGANISM: soybean
```

```
<400> SEQUENCE: 1

Ser Lys Trp Gln His Gln Gln Asp Ser Cys Arg Lys Gln Leu Gln Gly
1               5                   10                  15

Val Asn Leu Thr Pro Cys Glu Lys His Ile Met Glu Lys Ile Gln Gly
                20                  25                  30

Arg Gly Asp Asp Asp Asp Asp Asp Asp Asp
            35                  40
```

MODULATING INNATE IMMUNE CELL ACTIVITY BY LUNASIN AND SELECTED CYTOKINES

CROSS-REFERENCE TO RELATED APPLICATIONS

This application is a US National Phase filing of PCT/US2012/040144, filed on May 31, 2012, which claims benefit of US 61/491,450, filed on May 31, 2011. The disclosure of which is expressly incorporated entirely by reference.

FIELD OF INVENTION

This invention relates to the use of lunasin and other selected cytokines in conjunction with their broad application over innate immune system responses. Particularly, lunasin demonstrated robust synergy on certain selected cytokine effect on innate immune cells.

BACKGROUND

The innate immune system comprises cells and mechanisms that defend the host from infection by other organisms in a non-specific manner. In addition to the role as the first line of defense against infection, the innate immune response plays a vital role in killing cancerous cells. Natural killer (NK) cells, a key component of the innate immune response, represent 10-15% of-circulating lymphocytes in the blood. NK cells possess potent cytolytic activity against virus- or pathogen-infected cells and tumor cells by releasing cytotoxic granules that can spontaneously kill target cells. NK cells also possess immunoregulatory functions that influence adaptive immunity by modulating the activity of other immune cells. Aberrant immune responses can lead to excessive inflammation and autoimmune reactions, leading to diseases such as arthritis and allergies. Therefore, modulation of NK cells could lead to a more robust or properly regulated immune response, enhancing immune response to infected cells, enhanced tumor clearance, decreased inflammatory and allergic responses, and increase efficacy of cancer vaccines.

Given its critical role in immunity and tumor targeting, several strategies for the therapeutic use of NK cells has been proposed and tested. Adoptive transfer of NK cells from autologous or allogeneic donors have been used in the clinic to neat various types of cancers, with mixed results. Attempts to enhance the activity of NK cells for adoptive transfer have treated the cells with cytokines, such as IL-2 and IL-12, prior to injecting the cells into the patient. Adoptive transfer of NK cells to make them more active also has been attempted via genetic manipulation of the NK cells prior to injection into patient. Adoptive transfer poses technical and safety concerns, such as increased risk of spreading disease from the donor to host, intense donor screening and selection, technical expertise in handling and manipulation of the cells, great expense, and potential long term health risks to the patient.

Other strategies to manipulate NK activity that has been pursued are the use of immunomodulatory drugs such as thalidomide and cytokines such as IL-2, IL-12, IL-15, IL-18, IL-21 and type I IFNs, to stimulate the patients endogenous NK cells. However, toxicity of cytokines in high doses required for effective stimulation of NK cells prohibits then systemic administration. As such, a novel strategy for activating NK cells with better efficacy and less toxicity is warranted, and described within.

BRIEF SUMMARY

Thus disclosure provides a combination therapy composed of lunasin and at least one cytokine. The combination therapy enhances the at least cytokine's effect on an innate immune system. In the combination therapy, the at least one cytokine is selected from the group consisting of IL-2, IL-12, IL-15, IL-18, IL-21 and IFN-α.

In some preferred embodiment, the combination therapy enhances innate immune system expression of IFN-γ, IL-15, CCL2, CCL3, CCL4 or GM-CSF.

In some preferred embodiment, the combination therapy attenuates the suppression of Th1 switch.

In some preferred embodiment, the combination therapy enhances the innate immune system's ability to eliminate viral-infected cells and other pathogens.

In some preferred embodiment, the combination therapy enhances natural killer (NK) cell cytotoxicity by increasing expression of Granzyme B and natural cytotoxicity triggering receptor 2 (NCR2).

In some preferred embodiment, the combination therapy enhances NK cell cytotoxicity by decreasing expression of inhibitory killer-cell immunoglobulin-like receptors (KIR).

In some preferred embodiment, the combination therapy enhances antibody-dependent cell mediated cytotoxicity (ADCC) by NK cells.

In one preferred embodiment, the combination therapy stimulates NK cells to enhance adoptive transfer cellular therapy.

In some preferred embodiment, the combination therapy is an adjuvant to enhance efficacy of a cancer vaccine.

This disclosure provides a method of enhancing an innate immune system, the method comprising providing an individual with a pharmaceutically effective amount of a combination of lunasin and at least one cytokine. In some preferred embodiment, the at least one cytokine is selected from the group consisting of IL-2, IL-12, IL-15, IL-18, IL-21 and IFN-α.

In another preferred embodiment, the at least one cytokine is IL-2 or IL-12.

In another preferred embodiment, the at least one cytokine is IL-12.

In another preferred embodiment, the at least one cytokine is IL-18.

In another preferred embodiment, the enhanced immune system has natural killer (NK) cells with increased expression of natural cytotoxicity triggering receptor 2 (NCR2) and Granzyme B.

In another preferred embodiment, the enhanced immune system has NK cells with decreased expression of killer-cell immunoglobulin receptors (KIR).

In another preferred embodiment, the enhanced immune system has NK cells with an enhanced immune regulatory effect on allergic inflammation.

In another preferred embodiment, the enhanced immune system has NK cells with increased antibody dependent cell mediated cytotoxicity (ADCC).

This disclosure further provides a method of enhancing activity of natural killer (NK) cells, the method comprising providing an individual with a pharmaceutically effective amount of a combination of lunasin and at least one cytokine. In some preferred embodiments, the aforementioned cytokine is IL-12 or IL-2. In some preferred embodiments, the NK cells have increased expression of Granzyme B or natural cytotoxicity triggering receptor 2 (NCR2).

This disclosure further provides a method of increasing natural killer (NK) cell immune regulatory effect on allergic inflammation, the method comprising providing an individual with a pharmaceutically effective amount of a combination of lunasin and at least one cytokine. In some preferred embodiments, the aforementioned cytokine is IL-12 or IL-2.

In some of preferred embodiments, the NK cells have increased expression of Granzyme B or natural cytotoxicity triggering receptor 2 (NCR2).

This disclosure further provides a method of increasing antibody dependent cell mediated cytotoxicity (ADCC) by natural killer (NK) cells, the method comprising providing an individual with a pharmaceutically effective amount of a combination of lunasin and at least one cytokine. In some of preferred embodiments, the NK cells have increased expression of Granzyme B or natural cytotoxicity triggering receptor 2 (NCR2).

This disclosure further provides a method of treating virus-infected cells in an individual, the method comprising providing the individual with a pharmaceutically effective amount of a combination of lunasin and at least one cytokine. In some preferred embodiments, the cytokine is IL-18.

This disclosure further provides a method of enhancing efficacy of a cancer vaccine, the method comprising providing an individual a pharmaceutically effective amount of a combination of lunasin and at least one cytokine.

In some of the preferred embodiments for any of aforementioned methods, the at least one cytokine is selected from the group consisting of IL-2, IL-12, IL-15, IL-18, IL-21 and IFN-α.

These and other features, aspects and advantages of the present invention will become better understood with reference to the following figures, associated descriptions and claims.

DETAILED DESCRIPTION

Figure 1:
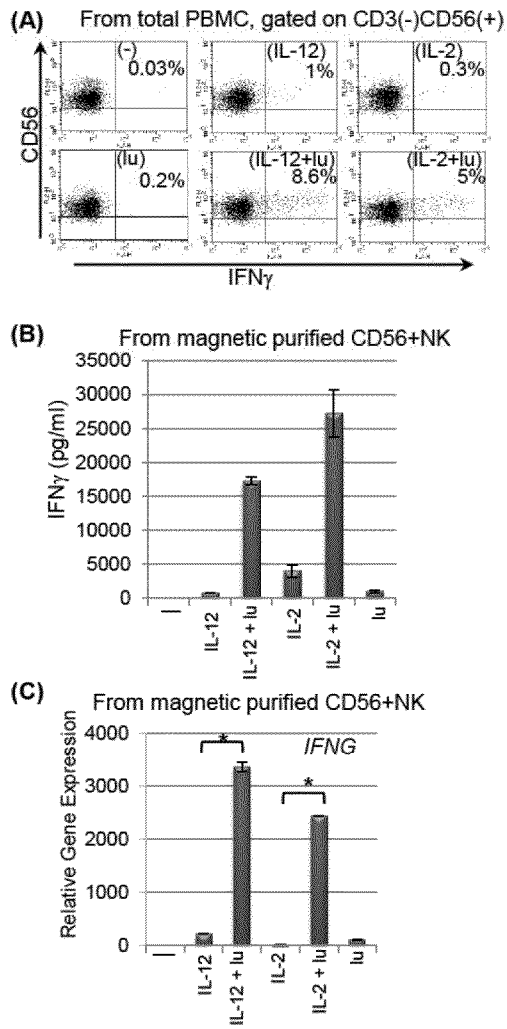
FIG. 1 IFNγ production by primary NK cells following stimulation. Human primary NK cells were isolated from peripheral blood mononuclear cells (PBMCs) of normal controls using positive selection with CD56 magnetic beads (Miltenyi Biotec Auburn. CA). Freshly isolated NK cells were stimulated with medium only (−) lunasin only at 20 μM (lu) cytokine IL-12 at 10 ng/ml or IL-2 at 100 units/ml and cytokine with lunasin for 1 day (A) Intracellular cytokine staining of IFNγ production by human NK cells using flow cytometry. At the last 6 hrs of stimulation, golgistop (monensin) was added to block the secretion of IFNγ. Stimulated PBMCs were surface stained with FITC-conjugated CD3 and PE-congugated CD56 monoclonal antibodies (BD), washed, fixed, and permeabilized. After washing, cells were incubated with APC-conjugated anti IFNγ monoclonal antibody. Expression of IFNγ was evaluated on 5000 events of gated CD3 negative and CD56 positive NK cell populations. The % of NK populations producing IFNγ is labeled at the upper right quadrant of the dot plot. (B) IFNγ production in the supernatants. One day following stimulation, the supernatants were collected for measuring the concentrations of IFNg using ELISA. Results are presented as mean±SD from duplicates. (C) IFNG gene expression. The cell pellets from (B) were analyzed for gene expression using qPCR with Taqman Assay primers. Data are presented as mean±SD from duplicates. Results shown are representative from over 5 normal controls.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to tins disclosure. We propose a term "lunakine" as a combination of lunasin and a selective cytokine in which the lunakine demonstrates synergistic effect of the selective cytokine on certain innate immune cells. Generally, the procedures for cell culture, infections, molecular biology methods and the like can be found in the art.

Overview of Innate Immune Cells

The innate immune system, also known as non-specific immune system and first line of defense, comprises the cells and mechanisms that defend the host from infection by other organisms. This means that the cells of the innate system recognize and respond to pathogens in a generic way. Unlike the adaptive immune system, it does not confer long-lasting or protective immunity to the host. Innate immune systems provide immediate defense against infection, and are found in all classes of plant and animal life.

The major functions of the vertebrate innate immune system include: recruiting immune cells to sites of infection through the production of chemical factors, including specialized chemical mediators called cytokines; activation of the complement cascade to identify bacteria, activating cells and to promote clearance of dead cells or antibody complexes; the identification and removal of foreign substances present in organs, tissues, the blood and lymph, by specialized white blood cells; activation of the adaptive immune system through a process known as antigen presentation; acting as a physical and chemical barrier to infectious agents.

Inflammation is one of the first responses of the immune system to infection or irritation. Inflammation is stimulated by chemical factors released by injured cells and selves to establish a physical barrier against the spread of infection, and to promote healing of any damaged tissue following the clearance of pathogens.

The process of acute inflammation is initiated by cells already present in all tissues, mainly resident macrophages, dendritic cells, histiocytes, Kupffer cells and mastocytes. These cells present on their surfaces certain receptors named pattern recognition receptors (PRRs), which recognize molecules that are broadly shared by pathogens but distinguishable from host molecules, collectively referred to as pathogen-associated molecular patterns (PAMPs). At the onset of an infection, burn, or other injuries, these cells undergo activation (one of their PRR recognizes a PAMP) and release inflammatory mediators responsible for the clinical signs of inflammation.

Cytokines produced by natural killer (NK) cells, dendritic cells (DCs) and macrophages of the innate immune system mediate the inflammatory response. These cytokines include IFNγ, IL-12, TNFα, GM-CSF, and IL-1β.

The complement system is a biochemical cascade of the immune system that helps, or "complements", the ability of antibodies to clear pathogens or mark them for destruction by other cells. The cascade is composed of many plasma proteins, synthesized in the liver, primarily by hepatocytes. The proteins work together to: trigger the recruitment of inflammatory cells; "tag" pathogens for destruction by other cells by opsonizing, or coating, the surface of the pathogen; forming holes in the plasma membrane of the pathogen, resulting in cytolysis of the pathogen cell, causing the death of the pathogen; rid the body of neutralized antigen-antibody complexes.

Cells involved in innate immune system including the followings: NK cells, mast cells, eosinophils, basophils; and the phagocytic cells including macrophages, neutrophils and dendritic cells. Many of these cells function within the immune system by identifying and eliminating pathogens that might cause infection.

Natural killer cells (also known as NK cells) are a type of lymphocyte (a white blood cell) and a component of innate immune system. NK cells play a major role in the rejection of tumors and cells infected by viruses. They kill cells by releasing small cytoplasmic granules of proteins called perforin and granzyme that cause the target cell to die by apoptosis (programmed cell death). NK cells also directly exert several immunoregulatory functions by secreting cytokines.

Macrophages are large phagocytic leukocytes, which are able to move outside of the vascular system by moving across the cell membrane of capillary vessels and entering the areas between cells in pursuit of invading pathogens. In tissues, organ-specific macrophages are differentiated from phagocytic cells present in the blood called monocytes. Macrophages are the most efficient phagocytes, and can phagocytose substantial numbers of bacteria or other cells or microbes. The binding of bacterial molecules to receptors on the surface of a macrophage triggers it to engulf and destroy the bacteria through the generation of a "respiratory burst", causing the release of reactive oxygen species. Pathogens also stimulate the macrophage to produce chemokines, which summons other cells to the site of infection.

Dendritic cells (DC) are phagocytic cells present in tissues that are in contact with the external environment, mainly the skin (where they are often called Laugerhans cells), and the inner mucosal lining of the nose, lungs, stomach and intestines. They are named for their resemblance to neuronal dendrites, but dendritic cells are not connected to the nervous system. Dendritic cells are very important in the process of antigen presentation, and serve as a link between the innate and adaptive immune systems.

Neutrophils, along with two other cell types; eosinophils and basophils, are known as granulocytes due to the presence of granules in their cytoplasm, or as polymorphonuclear cells (PMNs) due to their distinctive lobed nuclei. Neutrophil granules contain a variety of toxic substances that kill or inhibit growth of bacteria and fungi. Similar to macrophages, neutrophils attack pathogens by activating a respiratory burst. The main products of the neutrophil respiratory burst are strong oxidizing agents including hydrogen peroxide, free oxygen radicals and hypochlorite. Neutrophils are the most abundant type of phagocyte, normally representing 50to 60% of the total circulating leukocytes, and are usually the first cells to arrive at the site of an infection. The bone marrow of a normal healthy adult produces more than 100 billion neutrophils per day, and more than 10 times that many per day during acute inflammation.

NK and Immunesurveillance

Despite the hostile environment that contributes to the epigenetic and genetic alterations, cancer immunosurveillance of the immune system is capable of recognizing and eliminating continuously arising, nascent transformed mutant cells. Both innate and adaptive immune cells act as sentinels in confining these malignant cells to a state that can be controlled. Preclinical studies have unequivocally shown that vertebrate immune system can recognize and destroy malignant tumor cells in vivo. Moreover, adoptive cellular therapy after allogeneic hematopoietic stem cell transplantation has provided proof-of-principle that the immune system can eradicate tumor cells in humans.

Innate immunity is mediated by effector cells, including NK cells and macrophages that can respond immediately before adaptive immunity being developed. NK cells represent 10-15% of circulating lymphocytes in blood, which exert a potent cytolytic activity against virus-infected or tumor cells by releasing cytotoxic granules. NK cells have the ability to spontaneously kill target cells without any prior immunization or stimulation.

Innate immune responses are rapid, and can provide a jump start to respond to a danger signal before the development of adaptive immunity. For example, NK cells use granzyme B, a serine protease, to exert their cytotoxic function, which are important in immune surveillance. Granzyme B is constitutively expressed in NK cells, and can be further upregulated by cytokines including IL-2 and IL-12.

NK and Cytotoxicity

The cytotoxicity of NK cells can be activated by interferon and cytokines (e.g., IL-12) that are produced by monocytes or dendritic cells (DC). In addition, activated NK cells result in the production of inflammatory cytokines (e.g., IFNγ and TNFα), mediators, and enzymes (e.g., granzyme B) that contribute to the eradication of tumor cells.

The killing activity of NK cells is regulated by the net signaling events triggered by invariant activating and inhibitory receptors that recognize the ligands on target cells. NK cells have two major classes of surface receptors: activating and inhibiting receptors. The activating receptors involved in NK-mediated cytolysis are NKG2D and the natural cytotoxicity receptors (NCRs) including NCR1 (NKp46 or CD335), NCR2 (NKp44 or CD336), and NCR3 (NKp30 or CD337). The inhibiting receptors include many of the killer-cell immunoglobulin-like receptors (KIR) on NK cells recognize MHC class I ligands on target cells, which inhibit NK cell-mediated cytotoxicity.

The interaction of KIR on NK cells with MHC class I proteins on target cells is inhibitory. Thus if an NK cell binds to any bodily cell with high levels of MHC class I proteins, it is not activated, or more precisely, it is simultaneously activated and inhibited, and the inhibition prevails. If an NK cell binds to a cell with low levels of class I MHC proteins or none at all, it is activated and kills the cell without inhibitory signals. The activation requires binding of some ligand, possibly a carbohydrate moiety on the target cell, to an "Activation Receptor" protein on the surface of the NK cell. In the absence of an inhibitory signal, from KIR for MHC class I protein, this Activation Receptor generates a signal that allows the NK cell to execute its target.

The inhibitory signal is mediated by the MHC class I protein and therefore it might first appear that any cell in the body would be resistant to NK killing. Interestingly, however, many rumors and virus infected cells have reduced levels of MHC class I proteins. Indeed one of the viral strategies to evade the immune system is to repress expression of class I MHC proteins, thus reducing the likelihood that viral peptides will be presented to cytotoxic T cells. This works to the advantage of the virus by delaying or reducing the immune response. But by lowering the levels of class I MHC, the virus "attracts" the attention of NK cells that respond to the deficiency of class I proteins by killing the infected cell. Thus the characteristics of NK cells are useful in fighting the viruses that use the MHC-reduction strategy.

Receptors involved in NK mediated cytolysis are NKG2D and the natural cytotoxicity receptors. Natural Cytotoxicity Receptors (NCRs) are cell surface glycoproteins that activate NK cells after ligand interaction. NCR2 is an activating receptor that promotes cytotoxicity and cytokine release upon ligand binding via the adaptor molecule. NCR2 expression is absent on fresh peripheral blood NK cells but may be induced by IL-2 in culture. Therefore NCR2 is used as specific marker for activated NK cells. In HTV-patient NCR2 was found on a substantial percentage of NKs and promotes cytotoxicity against NCR2 ligand positive CD4+ T cells. Unfortunately NCR2L is induced by a part of the HTV-1 envelop protein gp41, resulting in a progressive CD4+ T cell depletion by NK cells, which is correlated to the increase of the virus load.

A substitute activation of NCR2 is in need to activate NK cells while avoiding virus gp41dependent NCRL induction.

NK and ADCC (Antibody-dependent Cellular Cytotoxicity)

The binding of the Fc region of IgG to specific receptors (Fc receptors) expressed on NK cells results in activating signals for cytotoxicity, which is called ADCC or antibody-dependent cellular cytotoxicity. The CD16 (FcγRIII) receptor complex expressed by NK cells is involved in ADCC. The development of therapeutic antibody has a great impact especially on human cancer therapy that is based on NK-mediated ADCC.

NK Secreted IFN γ in allergic inflammation

NK secreted IFN γ plays an important role in modulating allergic inflammation. The rising prevalence of allergic diseases has resulted in increased cost of health services and reduced productivity, which represents a significant medical and economic burden. T helper type 2(Th2)-mediated allergic inflammation is the major molecular mechanism underlying asthma and other allergic diseases. Cytokine such as IL-4 secreted by Th2 cells induces B cells for isotype class switching to IgE that binds other leukocytes such as mast cells and eosinophils. When activated, these cells rapidly release their characteristic granule contents and mediators that contribute to the disease manifestation. A shift of the Th1/Th2 balance toward Th2differentiation predisposes individuals to allergic diseases. It has been shown that the increased susceptibility for allergic disease is a consequence of prevalent intake of "healthy food" rich in antioxidant that suppresses IFNγ production, a hallmark of Th1 cytokine. Furthermore, western modern diet containing increased polyunsaturated fatty acid (PUFA) has been linked to the increase in asthma and allergic diseases because of suppressed Th1 differentiation that promotes Th2 immune responses. NK secreted IFNγ may skew the balance of Th2/Th1 so that reverse the allergic disease process.

Current Status of Cytokine Immunotherapy

Cytokine immunotherapy enhances the anti-tumor immunity and is now part of the therapeutic armamentarium for cancer treatment. Immunostimulatory cytokines, such as IL-12and IL-2, have had limited efficacy in lymphoma patients after chemotherapy followed by autologous stem cell transplantation. It has been reported that these heavily-treated patients have acquired deficiency of Signal Transducer and Activator of Transcription 4 (STAT4), which results in defective production of IFNγ following IL-12 immunotherapy.

Bioavailability of Lunasin.

Soybean products appear in a large variety of processed food as well as in cosmetics and personal care products. Soybean comprises bioactive components that have anticancer effects. Among the most studied substances, the Bowman-Birk protease inhibitor (BBI) inhibits proteases involved in carcinogenesis, and is currently in human trials as an anti-carcinogenic agent. Lunasin is a 43-amino acid soybean peptide that has chemopreventive properties capable of suppressing carcinogenesis via chromatin modification. Lunasin contains a poly-D carboxyl end with 8 D-residues and an RGD cell adhesion motif (bold) SEQ. ID. NO: 1 SKWQHQQDSCRKQLQGNLT-PCEKHIMEKIQGRGDDDDDDDD.

Lunasin is present in all genotypes of soybean and other natural products such as wheat. Significant levels of lunasin could be detected in the blood after oral consumption, demonstrating that lunasin survives digestion in the gastrointestinal tract. Furthermore, lunasin extracted from autoclaved soybean products or blood of rats fed with lunasin-enriched soy (LES) is still active as evidenced by inhibiting acetylation of histone H3 and H4. These findings demonstrate that lunasin is a promising chemopreventive agent as it is heat-stable and remains its bioactivity after boiling or intestinal digestion.

Lunasin is known to directly induce apoptosis of transformed cells. Lunasin has utility as a preemptive strategy as well as a potential therapeutic regimens.

This disclosure provides evidence that lunasin exerts additional effects imposed by selected cytokines to modulate innate immune cells, for example, NK cell activity. Complementary interventions using dietary botanical products are able to modulate the immune system. Lunasin exhibits immunostimulatory effects. Adding lunasin to the IL-12 or IL-2 exerts robust synergistic effects on regulating expression of several important genes by NK cells, which may harness tumor immunosurveillance. The combination of lunasin and cytokines cocktails (IL-12 plus IL-2) was capable of restoring IFNγ production by NK cells in post-transplant Non-Hodgkin's lymphoma patients who have immune dysfunction due to chemotherapy. In addition, NK cells stimulated with lunasin plus IL-2 have higher tumoricidal activity than those stimulated with IL-2 using in vitro and the xenograft mouse model.

Lunasin shows robust synergistic effects on selected cytokines when these cytokines are acted on certain innate immune cells, for example, human NK cells, various dendritic cells and macrophages. The synergistic effects of lunasin are broad, including but not limited to stimulating NK cells' essential for anti-tumor immunity, increasing IFNγ and granzyme B production, and natural cytotoxicity triggering receptor 2 (NCR2) expression to activate NK's killing mode, i.e., the increased tumoricidal activity of NK cells following stimulation with lunasin peptides and selected cytokines; switching on NK's anti-viral surveillance system, such as down regulating inhibitory receptors to stop the engagement of KIR to MHC-I class antigen, therefore terminating the inhibitory mode of NK when any anti-viral cytokine is used in combination of lunasin; further enhancing NK's ADCC effect when a selected cytokine with such effect is used in conjunction with lunasin, etc. Lunsin's synergistic effect on selected cytokine (or cytokine cocktails) is also demonstrated on the downstream effectors of cytokines, such as to skew the Th2/Th1 differentiation to reverse allergic immune disease progress. Lunasin treatment also reduces allergic inflammation in mouse models, symbolized as reduced production of allergic inflammatory cytokine, such as IL-4.

Elucidation of the cocktail of selected cytokines with lunasin may result in preemptive strategies for therapeutic prevention of cancer, immune modulation, and/or antiviral, antiallergic therapy alternatives.

Cancer Prevention

Cancer is the number-two killer of Americans. More than 1,400,000 new cases of cancer are diagnosed each year in the United States and approximately 560,000 patients die of cancer annually. The high morbidity and mortality of this disease represents a significant economic and medical burden. However, cancer is mostly a preventable disease. More than 20% of cancer incidents are preventable by consuming a healthy diet with more vegetables and fruits.

Various preventive strategies can be undertaken to keep cancer cells dormant. Dietary modification is an important approach to prevent cancer development. A short list of diet properties that relate to cancer prevention include anti-oxidation as a ROS scavenger, anti-inflammation as regulating expression of pro-inflammatory mediators; promoting anti-tumor immunity by activating immune cells; and epigenetic alterations by modulating DNA methylation and chromatin acetylation.

IFNγ is by far one of the most potent factors to activate cytotoxic T lymphocyte (CTL) cytotoxicity against tumor cell. In addition, IFNγ enhances the immunogenicity of tumor cells by upregulating the MHC class I and class II expression that allows them to be recognized and eliminated by CD8 and CD4 T lymphocytes, respectively. Both spontaneously arising and chemically-induced tumors are more common in IFNγ receptor-deficient and IFNγ-deficient mice compared to wild-type mice. Inhibition of IFNγ in vivo abrogates the ability of immunocompetent mice to reject transplanted syngeneic tumors. Moreover, IFNγ is required for the efficacy of several immunotherapeutic approaches in preclinical models. Strategically increase the production of IFNγ is one of the targets to effectively kill tumor and other virus.

Effects of Lunasin on Immune Cells.

Due to the significant levels of lunasin detected in the peripheral blood after oral consumption, we tested the lunasin peptides' immunomodulatory effects on human immune cells. We have demonstrated that lunasin and cytokine IL-12 or IL-2 have synergistic effects on human NK cells, including up-regulating IFNG (interferon γ), GZMB (granzyme B) and NCR2 (natural cytotoxicity receptor 2) as well as augmenting in vitro cytotoxicity.

IL-12, IFN-γ, and Cancer Immunotherapy

IL-12-based immunotherapy is one of the emerging therapeutic strategies to harness the power of the immune system to eradicate cancer cells. Chemotherapy is most often used as a systemic treatment to eliminate cancer cells. However, there are numerous instances where clinical results do not meet expectations, possibly due to unforeseen effects during chemotherapy as demonstrated in our study. Indeed, we found that chemotherapy-treated Non-Hodgkin's Lymphoma (NHL) patients are refractory to IL-12 immunotherapy due to profound deficiency of signal transducer and activator of transcription 4 (STAT4) that is required for IL-12-mediated biological function including IFNγ production. STAT4 deficiency may impair not only IL-12-based immunotherapy, but any therapeutic approach that requires optimal production of IFN-γ for effective anti-tumor immunity. Therefore, alternative strategy to achieve an efficacious anti-tumor activity after transplantation may require interventions that exploit other mechanisms of IFNγ production.

Treatment of PBMCs with both IL-12 and IL-18 can partially rescue IFNγ production in PBMCs of Non-Hodgkin's Lymphoma. (NHL) post-transplant. Moreover, NHL post-transplant patient PBMCs produce comparable levels of IFNγ when they are stimulated with PMA and ionomycin, a strong and non-physiological stimulus, suggesting they are capable of making IFNγ if with a proper stimulus. We explored bioactive food component using lunasin, a soy peptide, as alternatives to circumvent the deficiency of IFNγ production. While lunasin alone had moderate effects, the combination of IL-12 and lunasin peptides markedly increased IFNG gene expression in a dose-dependent manner. The levels of IFNγ in the supernatants determined using ELISA also confirmed these results. Human peripheral blood mononuclear cells (PBMCs) of normal controls were stimulated, and we found that NK but not CD4 or CD8 T populations respond to lunasin stimulation as evidenced by IFNγ production evaluated using intracellular cytokine staining. In addition, the combination of lunasin and IL-12 further enhances the production of IFNγ by purified NK cells. Given the fact that lunasin enters peripheral blood and retains its bioactivity, tins peptide exerts systemic effects on NK cells.

NK cells use granzyme B, a serine protease, to exert their cytotoxic function, which are important in immune surveillance. Granzyme B is constitutively expressed in NK cells, and can be further upregulated by cytokines including IL-2 and IL-12. We have shown granzyme B is regulated by lunasin in NK cells. qPCR was performed to evaluate its gene expression. Although the increased concentration of IL-12 had no further induction of GZMB, the combination of IL-12 and lunasin peptides readily increased the gene expression of GZMB.

The combination of lunasin and selected cytokine (a therapeutics together designated as lunakine) exerts robust synergistic effects on modulating expression of various genes that are important for NK functions. These results have demonstrated the in vitro responsiveness of freshly isolated human NK cells to a lunakine in which lunasin peptides are in combination with IL-12 or IL-2.

We have also shown that NK cells have augmented cytotoxic activity following stimulation with the combination of cytokine and lunasin peptides by in vitro cytotoxicity assay with the target cell Raji, a human B-lymphoma cell line. The presence of lunasin further enhanced the cytotoxic activity as compared to cytokine alone. Taken together, these results demonstrate the ability of lunasin peptide in combination with cytokine to enhance the cytotoxicity of NK cells.

Synergistic Effects of Lunasin with Other Cytokines

In addition to IL-12, we also found that lunasin exerts the synergistic effects with other cytokines including IL-2, IL-15, IL-18, IL-21 and IFNα, which are known cytokines to activate NK cells. The combination of IL-2 and lunasin peptides readily increased IFNγ production while IL-15, IL-18, IL-21 and IFNα had modest effects. In addition, production of IFNγ by NK cells treated with lunasin plus IL-2 is similar to that with lunasin and IL-12 over 3 days of incubation. Furthermore, augmenting expression of granzyme B was observed in NK cells following the combination of IL-2 and lunasin stimulation. Since IL-2 mediates its biological function independent of STAT4, the application of IL-2 and lunasin peptides is a potential alternative to enhance the cancer immunotherapy for NHL patients who acquire STAT4 deficiency.

Our results have supported the immunomodulatory activity of lunakine on NK cells. The combination of lunasin with selected cytokines, such as IL-12 or IL-2 is an alternative strategy for enhancing (1) the efficacy of cancer immunotherapy by augmenting IFNγ production, (2) the tumoricidal activity of NK cells by increasing granzyme B expression, and (3) the potential of therapeutic prevention for cancer by promoting NK-mediated anti-tumor immunity and adjuvanticity.

Lunasin on Modulating Allergic Airway Inflammation

Allergy is clinically defined as type I hypersensitivity that is caused by undesirable immune response to a normally harmless substance called allergen. Common allergens include pollen, animal dander, house dust mite, and a variety of food such as eggs and peanuts. Exposure to allergens triggers the allergic inflammatory responses that induce the production of IgE. Binding of IgE to innate immune cells (e.g., mast cell and eosinophils) leads to the release of granule contents including lipid mediators and histamine. All these are the characteristics of allergic reactions. Allergic diseases are associated with a range of conditions including allergic asthma, allergic rhinitis, food allergies, and allergic eczema. The recent escalation of allergic diseases may be attributable in part to changes in environment, lifestyle, and dietary components. It has been shown that the increased susceptibility for allergic disease is a consequence of prevalently intake of "healthy food" rich in antioxidant that suppresses IFNγ production.

Pathogenesis of Allergic Inflammation

Depending on the cytokine milieu in the inflamed tissues, CD4+ T lymphocytes have the plasticity to differentiate into distinct subsets of T helper (Th) cells that are characterized by the production of signature cytokines. IL-12 promotes the differentiation of T helper type I (Th1) cells that produce proinflammatory cytokine IFNγ, whereas IL-4 promotes the development of Th2 cells that secrete IL-4, IL-5 and IL-13. The developed T helper subsets acquire effector phenotypes that promote specialized inflammatory responses.

It is well-established that Th2-mediated inflammation is the major molecular mechanism underlying asthma and other allergic diseases. Cytokines produced by Th2 cells mediate the following effects that contribute to allergic diseases: 1) IL-4 induces B cell isotype class switching to IgE that binds and activates mast cells to release the granule contents; 2) IL-5 recruits and activates eosinophils; 3) IL-13 activates goblet cells to secrete mucus. On the contrary, Th1 cytokine IFNγ directs several immunoregulatory mechanisms that inhibit Th2differentiation. A shift in the Th1/Th2 balance with favor in Th2 differentiation can result in allergic diseases. Studies also implicate that skewing to Th1 response can suppress Th2-mediated allergic inflammation, and therefore prevent and control allergic diseases.

Natural Killer (NK) in Lung Inflammation

NK cells are another major population that produces IFNγ, and represent 10-15% of circulating lymphocytes in blood, which exert a potent cytolytic activity against virus-infected or tumor cells by releasing cytotoxic granules. NK cells directly exert several immunoregulatory functions by secreting cytokine IFNγ. IFNγ inhibits the development of Th2 lineage and facilitates Th1 differentiation. Isotype switching in B cells to IgG is enhanced by IFNγ that in rums inhibits the IgE production. Innate immune responses mediated by NK cells are rapid, and can provide a jump start to respond to a stimulatory signal before the development of adaptive immunity. Indeed, NK cells can rapidly produce IFNγ after only 4 hrs of stimulation. NK cells are normally present in human lung interstitium. In mice, pulmonary allergic sensitization induces NK cell accumulation in lung-draining lymph nodes and regulates airway eosinophilia in a murine model of asthma. All these features and the cytokine milieu created by IFNγ-producing NK cells may preferentially prevent the development of Th2-mediated allergic inflammation.

Intervention of Allergy

Immunotherapy has been shown to prevent deleterious allergic reaction by exposing patients to the allergens thereby reducing sensitivity. However, treatment is a lengthy procedure and not appropriate for everyone. Therefore, alternative strategy to achieve an efficacious anti-allergic inflammation may require interventions that exploit other mechanisms.

Dietary modification is able to exquisitely structure the immune system that results in the imbalance of Th1/Th2 inflammation. Certain dietary components have the ability to stimulate immune cells, making them more effective for immunomodulation by secreting cytokines, chemokines, and other inflammatory mediators. It has been observed that increased susceptibility for allergic diseases is likely due to increased intake of food rich in antioxidant that suppresses IFNγ production. Epidemiologic data have linked the increasing polyunsaturated fatty acid (PUFA) in western modern diet to the increase in asthma and allergic diseases because increased synthesis of prostaglandin E2 suppresses Th1 and promotes Th2 differentiation. On the other hand, daily consumption of whole milk reduces asthma risk in preschool children. Furthermore, therapeutic intervention of herbal medicine is in part due to their effects on modulating the Th1/Th2 development, which is a common practice for regulating a number of diseases. The Chinese herbal extracts MSSM-002 have been shown to exert anti-allergic airway hyper reactivity by suppressing production of Th2 cytokines. On the other hand, extracts of other Chinese herbs suppress secretion of Th1 cytokine IFNγ and promotes Th2-mediated immune response, which are used to control autoimmune diseases with the expense of increased susceptibility for allergy. These studies suggest that the immune system can be manipulated by dietary component, which has significant impact on human health.

We have found that lunasin has immunomodulatory effects on enhancing Th1 cytokine IFNγ production by NK cells. In addition, significant levels of bioactive lunasin could be detected in the lung and peripheral blood, suggesting this peptide could potential exert effects on NK cells to promote IFNγ production and restrain the influence of Th2 allergic inflammation.

NK cells are an important defense mechanism against tumor cells and various pathogens. However, by their immunoregulatory activity NK cells may diminish Th2-mediated inflammation that alleviates the allergic responses to allergens. The concept of modulating allergic inflammation by lunasin is novel.

Our studies have demonstrated that lunasin has immunomodulatory effects on NK cells to enhance the production of IFNγ, which creates the cytokine milieu that promotes Th1 differentiation. Lunasin stimulates NK cells to increase the production of IFNγ that may inhibit Th2 development, and therefore, suppress Th2-mediated allergic airway inflammation. Therefore, there is a use of soy peptide lunasin for prevention and/or treatment of asthma and other allergic diseases. We have revealed additional effect of lunasin other than chemopreventative property in which it exerts anti-allergic inflammation.

Microbial Organisms

Embodiments of the invention include compositions and related methods for enhancing innate immune response that can have broad protection against a variety of pathogens or potential pathogens. For example, bacterial pneumonia in a normal host occurs at a rate of 1I100persons/year, mostly in elderly adults and young children and can be caused by a variety of organisms. It is most commonly caused by *Streptococcus pneumoniae*, followed in frequency by encapsulated *Hemophilus influenzae*. Other bacteria such as enteric gram negatives, anaerobes, and *Staphylococcus aureus* are significant causes of pneumonia in specific settings, such as healthcare facilities. *Mycobacterium tuberculosis* is highly infectious, and historically was an important cause of mortality worldwide. It has mostly been controlled with antibiotics in the developed world, though multidrugresistant strains continue to cause problems and are classified as Category C bioweapon agents. *Legionella pneumophila* was first identified during an outbreak in Philadelphia in 1978, though it is now recognized to occur widely at a low endemic rate related to environmental sources. Also, fungal infections of the lungs can cause symptomatic disease in normal hosts. *Histoplasma capsulatum, Coccidiodes immitis, Blastomyces dermatitidis,* and *Cryptococcus neoformans* can all cause pneumonia related to local exposure to high environmental concentrations. Pneumonia due to these pathogenic fungi is usually self-limited in normal hosts. Some additional "atypical" microorganisms, such as mycoplasmas, account for a substantial fraction of additional pneumonias in normal hosts. It is contemplated that a composition of the present invention can provide a rapid, temporal protection against a spectrum of agents that can cause, for example pneumonia or other disease states. In certain aspects the present invention may be used in combination with a vaccination regime to provide an additional protection to a subject that may or is exposed to one or more pathogenic or potentially pathogenic organism.

There are numerous microbes that are considered pathogenic or potentially pathogenic under certain conditions. In certain aspects, the pathogenicity is determined relative to infection via the lungs. Bacterial microbes include, but are not limited to various species of the *Bacillus, Yersinia, Franscisella, Streptococcus, Staphylococcus, Pseudomonas, Mycobacterium, Burkholderia* genus of bacteria. Particular species of bacteria from which a subject may be protected include, but is not limited to *Bacillus anthracia, Yersinia pestis, Francisella tularensis, Streptococcus pnemoniae, Staphylococcus aureas, Pseudoinonas aeruginosa, Burkholderia cepacia, Corynebacterium diphtheriae, Clostridia* spp, *Shigella* spp., *Mycobacterium avium, M. intracellular, M. kansasii, M. paratuberculosis, M. scrofulaceum, M. simiae, M. habana, M. interjectum, M. xenopi, M. heckeshornense, M. szulgai, M. fortuitum, M. immunogenum, M. chelonae, M. marinum, M. genavense, M. haemophilum, M. celatum, M. conspicuum, M. malmoense, M. ulcerans, M. smegmatis, M. wolinskyi, M. goodii, M. thermoresistible, M. neoaurum, M. vaccae, M. palustre, M. elephantis, M. bohernicam* and *M. septicum*

EXAMPLES

Example 1

Lunasin's Effect on Nature Killer (NK) Cells

Lunasin is originally known for its chemopreventive property that has been demonstrated in cell cultures and mice models (ref). It is known that lunasin can be detected in the peripheral blood after oral consumption. However, the effects of lunasin on immune cells in the peripheral blood are largely unknown. In this study we have identified an additional effect of lunasin on enhancing anti-tumor immunity mediated by peripheral NK cells, supporting its potential as an immunomodulating agent in harnessing cancer immunosurveillance. In addition, we have developed an alternative strategy to induce IFNg production by NK cells using lunasin in combination with single cytokine or cytokine cocktails (IL-12 and IL-2). The combination of lunasin and selected cytokine (a therapeutics together designated as lunakine) exerts robust synergistic effects on modulating expression of a number of genes that are important for NK function, suggesting lunakine is superior to cytokine alone for enhancing the efficacy of cytokine immunotherapy.

Lunasin Stimulates NK Cells to Produce IFNg

To investigate the effects of lunasin on immune cells, peripheral blood mononuclear cells (PBMCs) from healthy donors were stimulated with or without lunasin in the presence or absence of cytokine IL-12 or IL-2. Because IL-12 and IL-2 are known to induce the expression of IFNG by NK cells, these two cytokines are included in the stimulation for comparison. Following 1 day of stimulation, distinct cell populations that respond to stimulation were evaluated using intracellular cytokine staining for IFNγ production. We found that CD4 and CDS T populations remained negative with all stimulus (data not shown), while nature killer (NK) populations had more positive staining for IFNγ following stimulation with both lunasin and cytokine IL-12 or IL-2 as compared to cytokine or lunasin alone (FIG. 1A). This finding was further confirmed by stimulation of purified human NK cells followed by analysis of secreted IFNγ in the supernatants using ELISA (FIG. 1B). Results showed that lunasin in combination with cytokine IL-12 or IL-2 markedly increased the production of IFNγ while lunasin alone had moderate effects. The mRNA expression of IFNG from the cell pellets of the same cultures correlated with the ELISA results (FIG. 1C). Consistent with intracellular staining, purified CD4+ or CD8+ T cells produced undetectable levels of IFNγ under the same stimulation as in NK cultures (data not shown). Our initial data suggested that human NK cells respond to lunasin stimulation, and lunasin works with cytokine IL-12 or IL-2 to induce the production of IFNγ.

FIG. 1 shows human primary NK cells produce robust amount of IFNγ in combination treatment with lunasin and IL-12 or IL-2. Aliquots of PBMCs isolated from healthy volunteer donors were cryopreserved in liquid nitrogen for the following assays. The lunasin peptides were commercially synthesized (LifeTein, South Plainfield, N.J.), and the 43-amino acid sequences are the following SEQ. ID. NO: 1: SKWQHQQDSCRKQLQGVNLT-PCEKHIMEKIQGRGDDDDDDDDD. (A) Intracellular cytokine staining of IFNγ production by human NK cells using flow cytometry. Peripheral blood mononuclear cells (PBMCs) of normal controls were stimulated with medium only (−), lunasin only at 20 μM (hi) cytokine IL-12 at 10 ng/ml or IL-2 at 100 units/ml, and cytokine with lunasin for 1 day. At the last 6 hrs of stimulation, golgistop (monensin) was added to block the secretion of IFNγ. Stimulated PBMCs were surface stained with FITC-conjugated CD3 and PE-conjugated CD56 monoclonal antibodies (BD), washed, fixed, and permeabilized. After washing, cells were incubated with APC-conjugated anti-IFNγ monoclonal antibody. Expression of IFNγ was evaluated on 5000 events of gated CD3 negative and CD56 positive NK cell populations. The % of NK populations producing IFN γ is labeled at the upper light quadrant of the dot plot. (B) IFNγ production in the supernatants. Freshly isolated human NK cells from peripheral blood mononuclear cells (PBMCs) of normal controls using positive selection with CD56 magnetic beads (Miltenyi Biotec, Auburn, Calif.) were stimulated as indicated. One day following stimulation, the supernatants were collected for measuring the production of IFNγ using ELISA. Results are presented as mean±SD from duplicates. (C) IFNG gene expression. The cell pellets were analyzed for gene expression using qPCR with Taqman Assay primers. Data are presented as mean±SD from duplicates. Results shown are representative from over 5 different normal controls.

Figure 2:
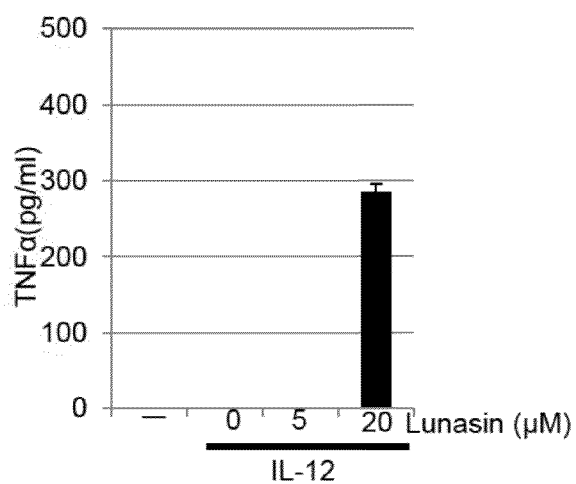
FIG. 2 TNF α production by primary NK cells following stimulation. Human primary NK cells were isolated from peripheral blood mononuclear cells (PBMCs)of normal controls using positive selection with CD56 magnetic beads (Miltenyi Biotac, Auburn CA). Freshly isolated NK cells were stimulated with medium only (−), IL-12 (10 ng/ml) in the absence (0) or presence of various concentrations of soluble lunasin peptides for 1 day. The supernatants were collected for measuring the concentrations of TNFα using ELISA. Results are presented as mean±SD from duplicates.

In addition to IFNγ, NK cells treated with IL-12 and lunasin also produce other cytokines. FIG. 2 shows TNFα production by primary NK cells isolated from normal controls following stimulation. Human primary NK cells were isolated from peripheral blood mononuclear cells (PBMCs) of normal controls using positive selection with CD56 magnetic beads (Miltenyi Biotec, Auburn, Calif.). Freshly isolated NK cells were stimulated with medium only (−), IL-12(10 ng/ml) in the absence (0) or presence of various concentrations of soluble lunasin peptides for 1 day. The supernatants were collected for measuring the concentrations of TNFα using ELISA. Results are presented as mean±SD from duplicates.

Figure 3:
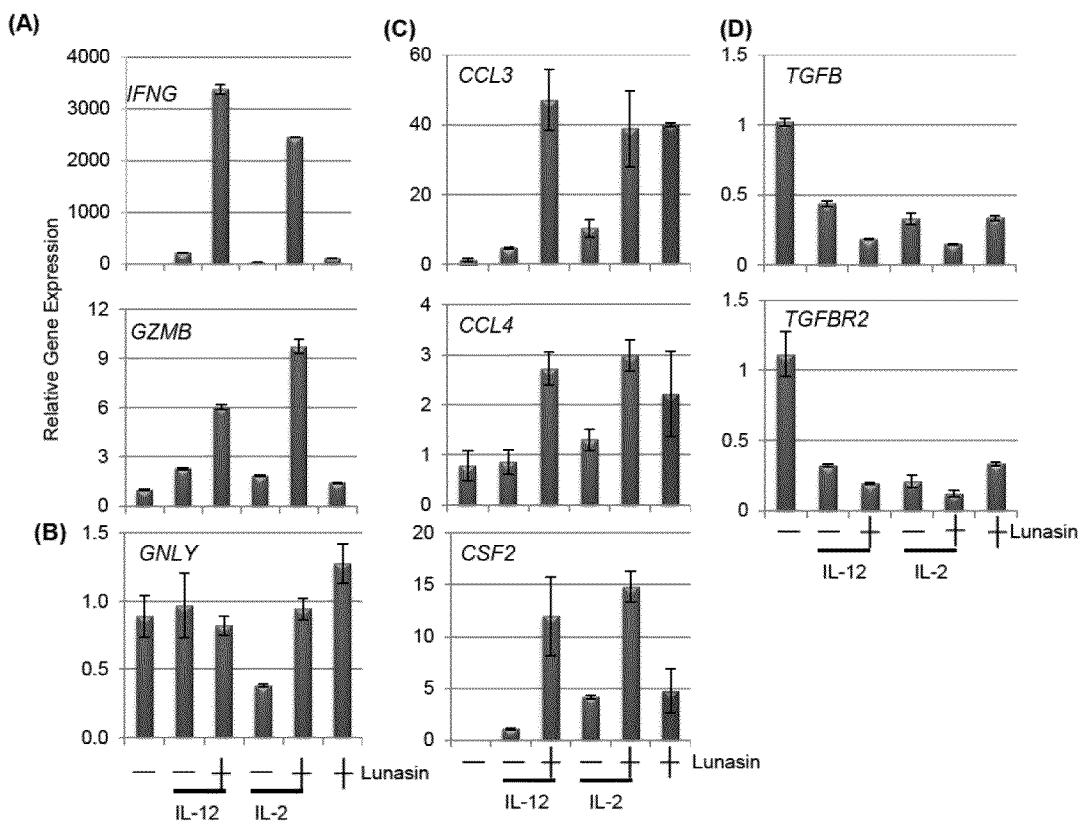
FIG. 3 Synergistic effects of lunasin and cytokines on gene expression by human primary NK cells. Freshly isolated human NK cells from peripheral blood mononuclear cells (PBMCs) of normal controls using positive selection with CD56 magnetic beads (Miltenyi Biotec, Auburn, CA)were stimulated with medium only(−), IL-12(10 ng/ml), IL-12 (10 ng/ml)+lunasin (20 mM), IL-2 (100 unit/ml), IL-2 (100 unit/ml)+lunasin (20 mM) or lunasin alone (20 mM). One day following the stimulation, the cell pellets were resuspended in Trizol Reagents for total RNA extraction. The first-strand cDNA was synthesized followed by real time qPCR using Taqman Assay with primers for IFNγ(IFNG), granzyme B (GZMB), granulysin (GNLY), chemokine (C-C motif) ligand 3 or CCL3 (CCL3), CCL4 (CCL4). Granulocyte-macrophage colony-stimulating factor or GM-CSF (CSF2) TGFβ (TGFB) and TGFβ receptor (TGFBR2) in ABI 7300 (Applied Biosystems by Life Technologies, Carlsbad CA) Data are presented as mean±SD from 2 duplicates. Results shown are representative over 5 different normal controls.

IL-12 and IL-2 are known cytokines to activate NK cells by regulating expression of a number of genes that are important for NK functions. Because of robust synergistic effects of lunasin with IL-12 or IL-2 on inducing IFNG expression, we next evaluated whether lunasin is able to modulate other target genes that are known to be regulated by cytokine IL-12 or IL-2. Results of qPCR from samples in FIG. 1C showed that adding lunasin to IL-12 or IL-2significantly increased expression of GZMB (granzyme B), while reduced TGFB1 (TGFβ1) and TGFBR2 (TGFβ receptor 2) as compared to those with cytokine alone (FIG. 3). Lunasin appeared to exert synergistic effects imposed by the selected cytokine IL-12 or IL-2 to modulate expression of target genes in NK cells. In addition, we also found that lunasin by itself is sufficient to up-regulate genes such as CCL3, CCL4 and CSF2 while no effects on GMT (FIGS. 3C and 3B).

FIG. 3 shows Synergistic effects of lunasin and cytokines on gene expression by human primary NK cells. Freshly isolated human NK cells from peripheral blood mononuclear cells (PBMCs) of normal controls using positive selection with CD56 magnetic beads (Miltenyi Biotec, Auburn, Calif.) were stimulated with medium only (−), IL-12 (10 ng/ml), IL-12 (10 ng/ml)+lunasin (20 μM), IL-2 (100 unit/ml), IL-2 (100 unit/ml)+lunasin (20 μM) or lunasin alone (20 μM). One day following the stimulation, the cell pellets were resuspended in Trizol Reagents for total RNA extraction. The first-strand cDNA was synthesized followed by real time qPCR using Taqman Assay with primers for IFNγ (IFNG), granzyme B (GZMB), granulysin (GNLY), chemokine (C-C motif) ligand 3 or CCL3 (CCL3), CCL4 (CCL4), Granulocyte-macrophage colony-stimulating factor or GM-CSF (CSF2), TGFβ (TGFB) and TGFβ receptor (TGFBR2) in ABI 7300 (Applied Biosystems by Life Technologies, Carlsbad, Calif.). Data are presented as mean±SD from duplicates. Results shown are representative over 5 different normal controls.

Lunasin is Shown to Down Regulate IFNγ's Negative Regulators

Figure 4:
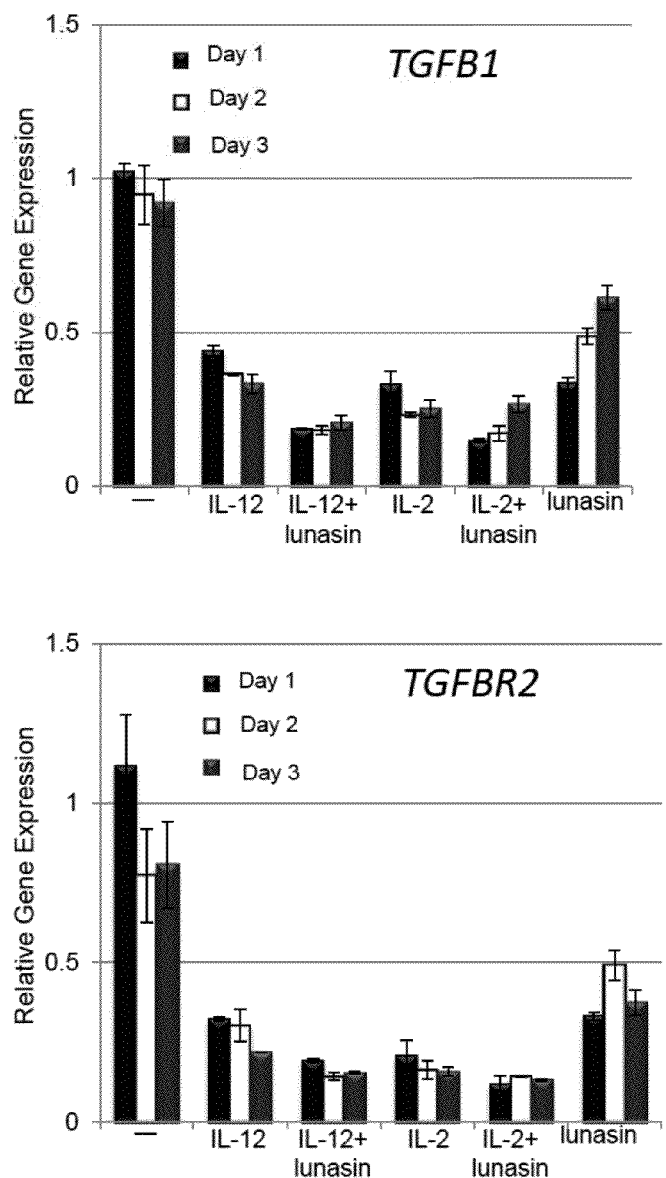
FIG. 4 Gene expression for TGF-b (TGFB1) and TGF-b receptor (TGFBR2) by human primary NK cells following stimulation over 3 days. Freshly isolated human NK cells from peripheral blood mononuclear cells (PBMCs) of normal controls using positive selection with CD56 magnetic beads (Miltenyi Biotec, Auburn, CA) were stimulated with medium only (−), IL-12 (10 ng/ml), IL-12(10 ng/ml)+lunasin(20 mM), IL-2 (100 unit/ml), IL-2 (100 unit/ml)+lunasin (20 mM) or lunasin alone (20 mM). Following 1, 2, and 3 days of stimulation, the cell pellets were lysed in Trizol Reagents for total RNA extraction. The first-strand cDNA was synthesized followed by real time qPCR using Taqman Assay with primer for TGFB 1 (upper panel) and TGFBR2 (lower panel) in ABI 7300. Results are presented as mean±SD from duplicates.

In FIG. 3, we observed a greater reduction of TGFB1 and TGFBR2 (TGF-β receptor II) in NK cells following IL-12/IL-2 and lunasin stimulation than those with medium only, cytokine or lunasin alone. FIG. 4 shows gene expression for TGF-β (TGFB1) and TGF-β receptor (TGFBR2) by human primary NK cells following stimulation over 3 days. Freshly isolated human NK cells from peripheral blood mononuclear cells (PBMCs) of normal controls using positive selection with CD56 magnetic beads (Miltenyi Biotec. Auburn, Calif.) were stimulated with medium only (−), IL-12 (10 ng/ml), IL-12 (10 ng/ml)+lunasin (20 μM), IL-2 (100 unit/ml), IL-2 (100 unit/ml)+lunasin (20 μM) or lunasin alone (20 μM). Following 1, 2, and 3 days of stimulation, the cell pellets were lysed in Trizol Reagents for total RNA extraction. The first-strand cDNA was synthesized followed by real time qPCR using Taqman Assay with primer for TGFB1 and TGFBR2 in ABI 7300. Results are presented as mean±SD from duplicates.

Because TGF-β1 is a negative regulator of IFNγ in NK cells, and deacetylation of histone H3 is associated with gene repression, we tested the hypothesis that lunasin inhibits TGFB1 or TGFBR2 expression by modulating chromatin structure of these gene loci in NK cells following IL-12/IL-2 and lunasin stimulation, and therefore IFNG expression is up-regulated because of less negative regulator TGF-β1 and unresponsiveness to TGF-β1 due to reduced expression of TGF-β receptor II.

To evaluate chromatin remodeling, freshly isolated human NK cells from peripheral blood mononuclear cells (PBMCs) of normal controls using positive selection with CD56magnetic beads (Miltenyi Biotec, Auburn, Calif.) were stimulated with medium only (−), IL-12 (10 ng/ml), IL-12 (10 ng/ml)+lunasin (20 μM) or lunasin alone (20 μM). Following 1 day of stimulation, cells were subjected to ChIP assay. Chromatin DNA fragments were immunoprecipitated with antibodies against acetyl-histone H3 (AcH3) and non-immune rabbit serum (Millipore, Billerica, Mass.), individually. The relative degree of histone acetylation of IFNG and TGFB1 loci was compared by qPCR using primers that amplify the promoter region (+1 kb). For quantification of chromatin immunoprecipitates, a standard curve was generated from a known amount of sonicated NK cell DNA. For calculation of ChIP results as a percentage of input, the amount of the immunoprecipitated DNA from the non-immune rabbit serum was subtracted from the amount of immunoprecipitated DNA from the AcH3 antibody, followed by normalizing against the amount of the input DNA. Data are shown as mean percentage of input±SD from duplicates.

Figure 5:
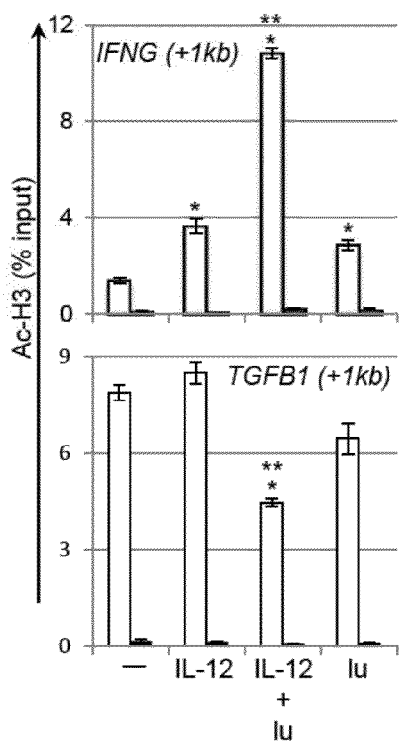
FIG. 5 Chromatin modification of IFNG and TGFB1 loci by lunasin, Freshly isolated human NK cells from peripheral blood mononuclear cells (PBMCs) of normal controls were stimulated with medium only (−), IL-12 (10 ng/ml), IL-12 (10 ng/ml)+Lunasin (20 μM) or lunasin alone (20 μM). Following 1 day of stimulation, cells were subjected to Chromatin Immunoprecipitation (ChIP) assay, Chromatic DNA fragments were immunoprecipitated with antibodies against acetyl-histone H3 (AcH3 open bar) and non-immune rabbit serum (filled bar) (Millipore, Billerica, MA), individually. The relative degree of histone acetylation of IFNG and TGFB1 loci was compared by qPCR using primers that amplify the promoter region (+1 kb). For quantification of chromatin immunoprecipitates, a standard curve was generated from a known amount for sonicated NK cell DNA. For calculation of ChIP results as a percentage of input, the amount of immunoprecipitated DNA is normalized to the input chromatin in each reaction. Data are shown as mean percentage of input±SD from duplicates. Results are representative from 3 different controls, *P<0.05, relative to NK stimulated with medium only (−). **P<0.05, relative to NK stimulated with IL-12 alone.

Epigenetic regulation by chromatin modification is known to alter gene expression, and deacetylation of H3 is associated with gene repression. Indeed, chromatin immunoprecipitation (ChIP)-qPCR demonstrated that greatly reduced acetyl-H3 is associated with TGFB1 locus in NK cells treated with lunasin plus IL-12 than IL-12 alone (FIG. 5A, lower panel). The synergistic effects of lunasin with selected cytokine such as IL-12 are in part due to reducing the levels of acetyl-H3, which further suppresses the expression of TGFB1. FIG. 5 shows Chromatin Immunoprecipitation (ChIP) assay for the chromatin structure of IFNG gene locus in NK cells following treatment, which is positively associated with acetylated histone H3 (FIG. 5A, upper panel). Results provides a mechanism of gene regulation in the example of IFNG in which lunasin down-regulates expression of negative regulators (e.g., TGFB1 and TGFBRII) that in mm up-regulate then corresponding target genes (e.g., IFNG).

Synergistic Effects of Lunasin with Other Cytokines

Figure 6:
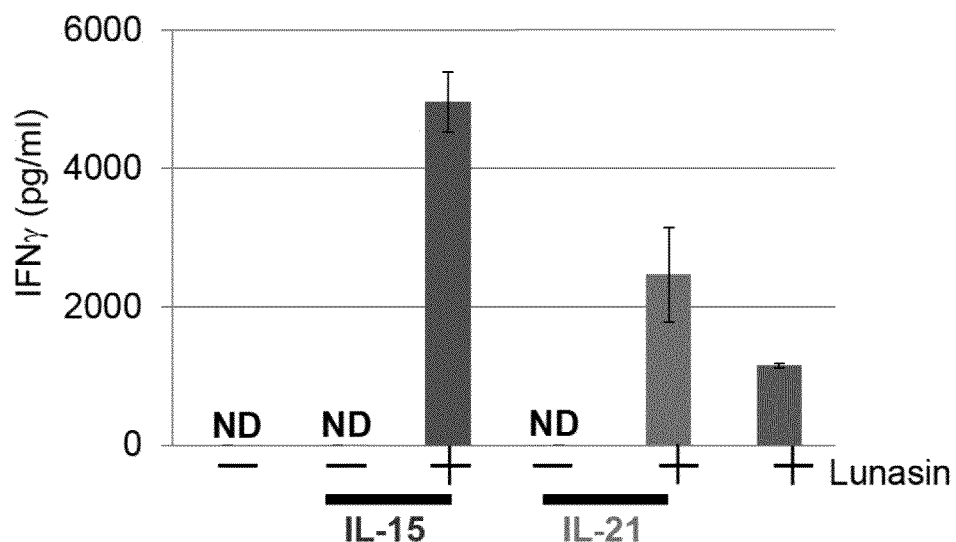
FIG. 6 Synergistic effects of lunasin with cytokine IL-15 or IL-21 on IFNγ production by human NK cells. Human primary NK cells were isolated from peripheral blood mononuclear cells (PBMCs) of normal controls using positive selection with CD56 magnetic beads (Miltenyi Biotec, Auburn CA). Freshly isolated NK cells were stimulated with medium only (−),IL-15(5 ng/ml) or IL-21 (10 ng/ml) in the absence (−) or presence of lunasin (20 μM), or lunasin alone (20 μM) for 1 day. The supernatants were collected for measuring the concentrations of IFNg using ELISA. Results are presented as mean±SD from duplicates.

Results using ChIP assay suggest that IL-2 or IL-12 initiates the chromatin remodeling that permits the access of lunasin peptide into the nucleosomes, which modulates histone modification for regulating expression of target genes. Other cytokines or agents capable of chromatin remodeling are therefore anticipated to grant the access of lunasin peptide for regulating gene expression. Indeed, we observed that the combination of IL-15, IL-18, IL-21 or IFNα with lunasin increases the expression of IFNγ production (FIG. 6).

Dose Dependent Effects of Lunasin on IFNγ Production

Because of the robust synergistic effects of lunasin with IL-12, we next tested: (1) if lunasin could reduce the concentrations of IL-12 while maintaining the efficacy on IFNγ production by NK cells; and (2) if this synergistic effect depends on the dose of lunasin. Human NK cells were stimulated with IL-12 at low (1 ng/ml) or high (10 ng/ml) or along with various concentrations of lunasin. Results demonstrated that IL-12 alone at high concentration is required to induce more IFNγ production than that with 10 fold lower concentration of IL-12 (FIG. 7A). However, in the presence of lunasin, lower concentration of IL-12 is capable of inducing IFNγ production to the levels comparable to those using 10 fold higher of IL-12, and this effect is dependent on the dose of lunasin (FIG. 7B).

Figure 7:
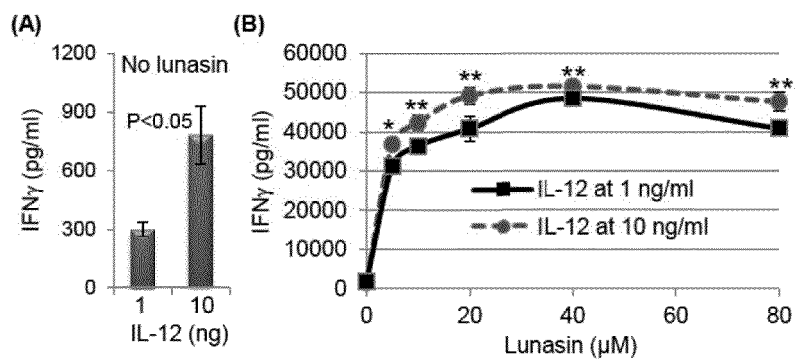
FIG. 7 Dose-dependent effects of lunasin on IFNγ production, Human NK cells isolated as described in FIG. 1 were stimulated with IL-12 at 1 or 10 ng/ml in the absence (A) or presence (B) of various concentrations of lunasin. One day following stimulation, The production of IFNg in the supernatants was determined using ELISA. Data are presented as mean±SD from 2 duplicates. Results shown are representative from over 3 different normal controls. *P<0.05,**>0.05.

FIG. 7 shows that responses of NK cells to lunasin in combination of IL-12 are dose dependent with IFNγ as the read out. Human primary NK cells were isolated from peripheral blood mononuclear cells (PBMCs) of normal control using positive selection with CD56magnetic beads (Miltenyi Biotec, Auburn, Calif.). Freshly isolated NK cells were stimulated with medium only (–), IL-12 alone (at 1 or 10 ng/ml), IL-12 (at 1 or 10 ng/ml) in the presence of various concentrations of lunasin peptides for 1 day. The supernatants were collected for measuring the production of IFNγ using ELISA. Results are presented as mean±SD from duplicates. Taken together FIG. 7 illustrates that it is lunasin that acts on NK cells to cause the dose dependent response of lunasin+IL-12 treatment.

Effects of Lunasin Plus Single Cytokine IL-12 or IL-2 on IFNγ Production by NK Cells with Acquired Stat4 Deficiency Following Chemotherapy in a Syngenic Tumor Mouse Model We previously reported that heavily-treated NHL patients acquired STAT4 deficiency as a consequence of chemotherapy, which contributes to impaired IFNγ production following IL-12immunotherapy. Since IL-2 mediates its biological function independent of STAT4 {Lin. 2000 #648} and lunasin works synergistically with IL-2 (FIGS. 1 and 3), we wanted to test whether IL-2 alone or the combination of lunasin and IL-2 can circumvent the deficiency of IFNγ produced by NK cells that are refractory to IL-12 stimulation due to chemotherapy-induced STAT4 deficiency. In our mouse model reduced Stat4 was found in NK cells from tumor-bearing mice following chemotherapy with etoposide. As expected, Stat4-defective NK cells secreted less IFNγ than those from Stat4-sufficient cells following IL-12 stimulation (FIG. 8A, filled bars). Adding lunasin to the IL-12 culture increased IFNγ production by NK cells from mice without chemotherapy (–etoposide) while no effects on those with reduced Stat4 following chemotherapy (+etoposide). Despite the potential independence of Stat4 mediated by the IL-2signaling pathway, Stat4-deficient NK cells did not respond to IL-2 stimulation, which resulted in undetectable levels of IFNγ production (FIG. 8B, filled bars). However, combination of lunasin with IL-2 was able to induce the production of IFNγ by Stat4-deficient NK cells, albeit at a lower level than those without Stat4 deficiency (FIG. 8B, open bars).

Dose-dependent Effects of Lunasin in Combination with Both Cytokines IL-12 and IL-2

Figure 9:
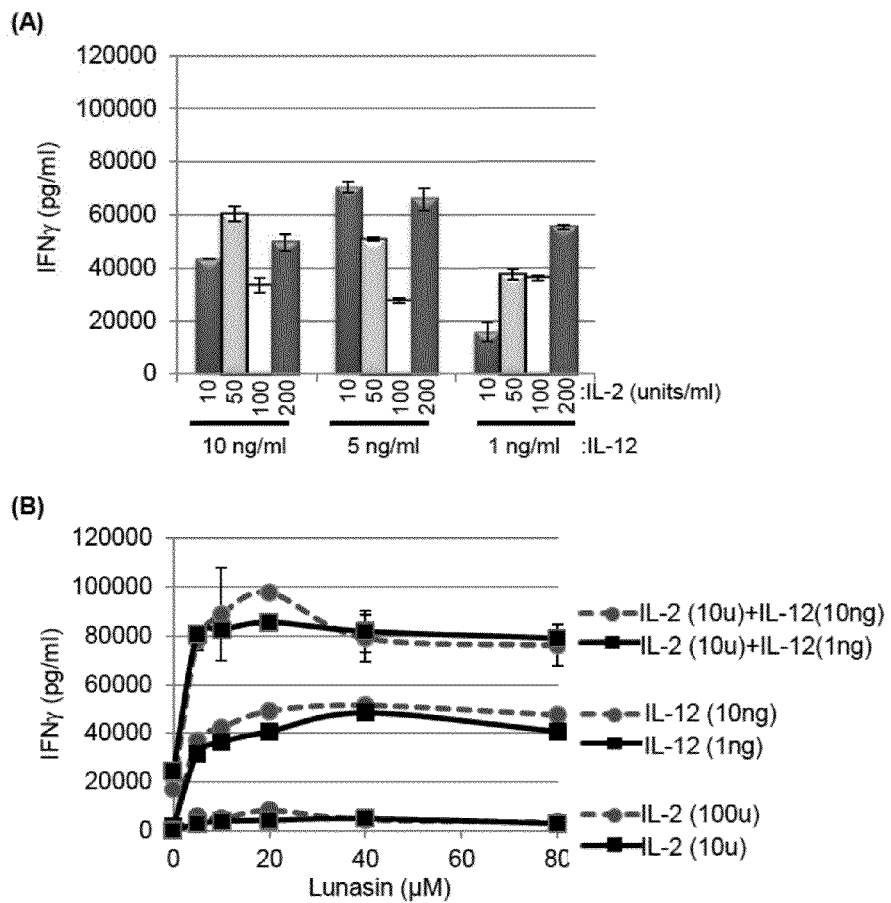
FIG. 9 Dose-dependent effects on IFNγ production using lunasin in combination with both cytokines IL-12 and IL-2. Human NK cells isolated as described in FIG. 1 were stimulated with various concentrations of IL-12 and IL-2 the absence (A) or presence (B) of various concentration of lunasin. One day following stimulation. The production of IFNg in the supernatants was determined using ELISA. Data are presented as mean±SD from duplicates. Results shown are representative from over 3 different normal controls.

Combination therapy of IL-12 and IL-2 induces potent anti-tumor immunity and is currently in clinical trial. Since adding lunasin to single cytokine did not result in successful recovering of IFNγ production by NK cells with acquired Stat4 deficiency in our mouse model, we wanted to test whether combination therapy with IL-12 and IL-2 in the presence of lunasin can circumvent such deficiency for rescuing IFNγ production. We next evaluated the production of IFNγ by normal NK cells following exposure to different concentrations of IL-12 and IL-2 to define the dose-response relationship. We found that at higher concentrations of IL-12 (5 and 10 ng/ml), adding IL-2 as little as 10 units/ml had significantly increased the production of IFNγ as compared to IL-12 alone, and the response was less dependent on the dose of IL-2 (FIG. 9A). When lowest concentration of IL-12 was used (at 1 ng/ml), the production of IFNγ increased in the presence of higher dose of IL-2. Combining both IL-12 and IL-2 even at the lowest doses significantly enhanced the levels of IFNγ as compared to those stimulated with single cytokine (FIG. 9A).

We next wanted to test the effects of adding various concentrations of lunasin to both cytokines on IFNγ production by NK cells. Levels of IFNγ were significantly higher in NK cultures with both cytokines IL-12 and IL-2 in the presence of lunasin than those without lunasin (FIG. 9B). Adding lunasin synergistically enhanced IFNγ production by NK cells stimulated with both cytokines IL-12 and IL-2 combined at various concentrations. The induction of IFNγ depends on the dose of lunasin, which appeared to reach the plateau in the presence of lunasin at 20 μM. Thus, adding lunasin to NK cultures can enhance IFNγ production following stimulation with lower concentrations of both cytokines IL-12 and IL-2, which may reduce the toxicity associated with the use of these cytokines.

Although IL-2 is approved by FDA, its toxicity in high doses prohibits the systemic administration. Because IL-2 and lunasin peptides act synergistically on inducing IFNγ production by NK cells, a lower dose of IL-2 is likely to achieve the same effects on IFNγ production in the presence of lunasin peptides. Similar combination of lunasin with other selective cytokine may be used to boost the desired IFN-γ production.

Example 2

The Effects of Lunasin on Cytokine Immunotherapy for Lymphoma Patients

Figure 8:
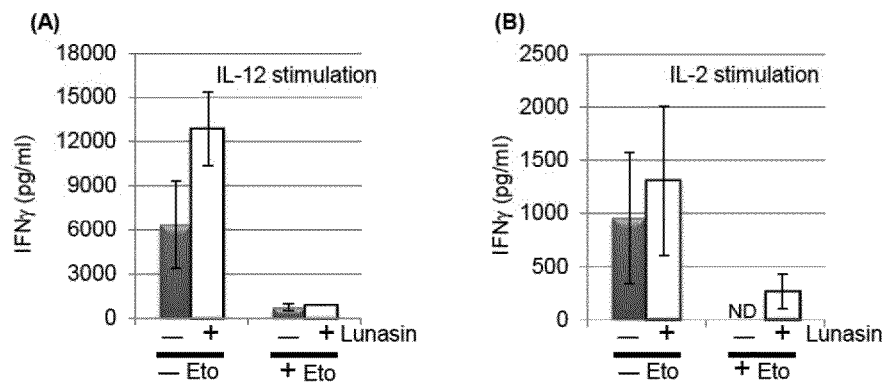
FIG. 8 IFNg produced by NK cells from tumor-bearing mice with or without chemotherapy. Mouse NK cells were positively selected from spleens of tumor-bearing mice with (+Eto) or without (−Eto) chemotherapeutic drug etoposide. Isolated NK cells were stimulated with mouse IL-12 at 2 ng/ml with (+) or without (−) lunasin peptide (A) or human IL-2 at 50 units/ml with (+) or without (−) lunasin at 20 μM (B). The production of IFNγ in the supernatant after 1 day of stimulation was determined using ELISA. Results are presented as mean±SD from 3 mice. ND is not detectable.
Figure 10:
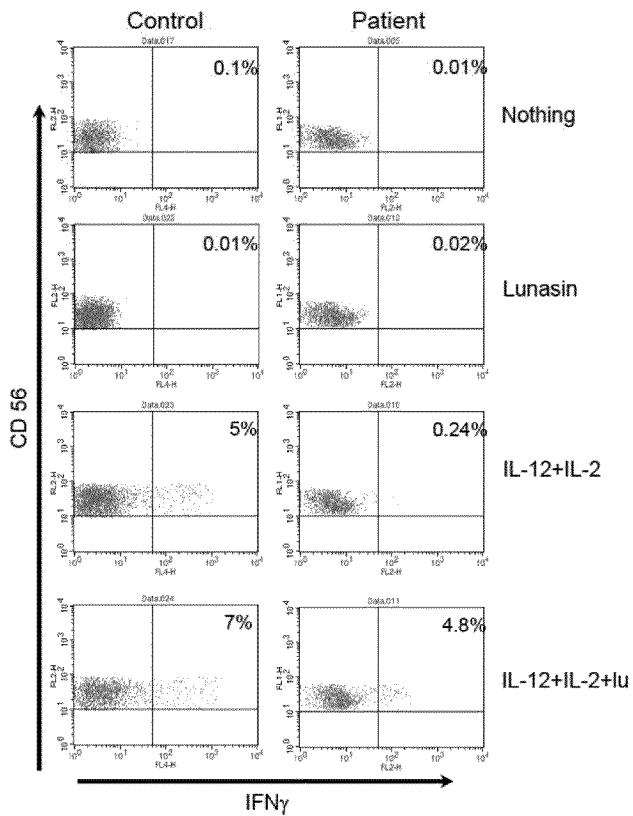
FIG. 10 Intracellular cytokine staining of IFNγ production by NK cells from post-transplant NHL patients. Peripheral blood mononuclear cells (PBMCs) of normal controls and post transplant NHL patients were stimulated with medium only (−), lunasin only at 20 μM (lu), IL-12 at 10 ng/ml and IL-2 at 100 units/ml, or both cytokine with lunasin for 1 day. At the last 6 hrs of stimulation, golgistop (monensin) was added to block the secretion of IFNγ. Stimulated PBMCs were surface stained with FITC-conjugated CD3 and PE-conjugated CD56 monoclonal antibodies (BD), washed, fixed, and permeabilized. After washing, cells were incubated with APC-conjugated anti-IFNγ monoclonal antibody. Expression of IFNγ was evaluated on 5000 events of gated CD3 negative and CD56 positive NK cell populations using flow cytometry. The % of NK populations producing IFNγ is labeled at the upper right quadrant of the dot plot.

Effects of Lunasin Plus Both Cytokines IL-12 and IL-2 on IFNγ Production by NK Cells from NHL Patients Post-Transplant Our results in FIG. 8 suggest the limited efficacy of lunasin in combination with single cytokine on inducing IFNγ production by NK cells with reduced Stat4 following chemotherapy. Because the unprecedented induction of IFNγ by adding lunasin to combination cytokines IL-12 and IL-2, we next tested the effects of this intervention on IFNγ production by post-transplant NHL NK cells ex vivo. As reported previously, STAT4 deficiency was observed in post-transplant patient PBMCs. Stimulation of patient PBMCs with both cytokines IL-12 and IL-2 resulted in positive production of IFNγ by NK populations (CD3-CD56+) using intracellular staining, albeit at a much lower % as compared to cells from normal controls (FIG. 10). However, adding lunasin to the stimulation can further increase the % of patient NK cells that produce IFNγ, which is similar to the level from normal controls. Thus, lunasin may enhance the clinical outcomes when used in combination with both cytokines IL-12 and IL-2.

Example 3

The Tumoricidal Activity of Lunasin-Stimulated NK Cells

Figure 11:
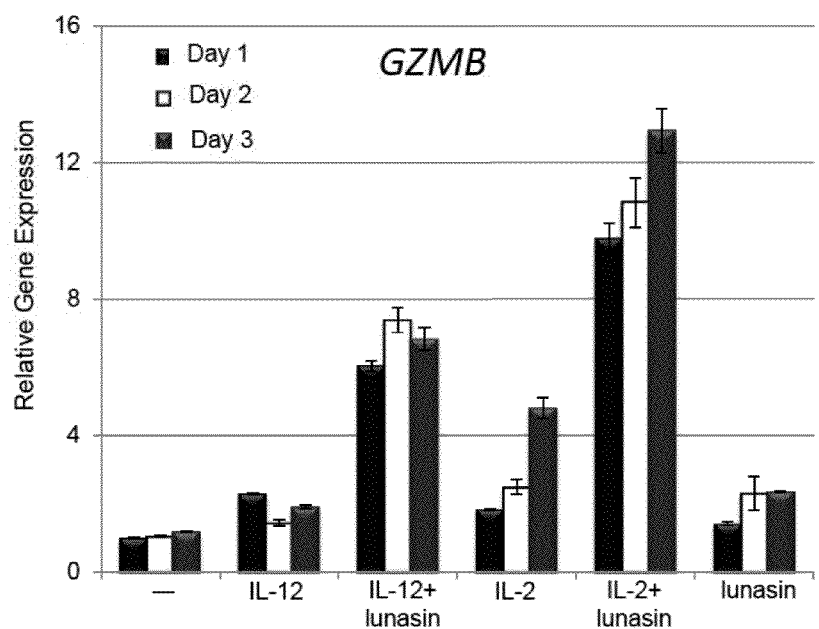
FIG. 11 Granzyme B gene expression (GZMB) by human primary NK cats following stimulation over 3 days. Freshly isolated human NK cells from peripheral blood mononuclear cells (PBMCs) of normal controls using positive selection with CD56 magnetic beads (Miltenyi Biotec Auburn, CA) were stimulated with medium only (−) IL-12 (10 ng/ml). IL-12 (10 ng/ml)+lunasin(20 mM), IL-2(100 unit/ml), IL-2 (100 unit/ml)+lunasin(20mM) or lunasin alone (20 mM). Following 1, 2, and 3 days of stimulation, the cell pellets were lysed in Trizol Reagents for total RNA extraction. The first-strand cDNA was synthesized followed by real time qPCR using Taqman Assay with primer for granzyme B (GZMB) in ABI 7300. Results are presented as mean±SD from 2 duplicates.

In addition to an immunoregulatory role of NK cells through cytokine production, they have the ability to spontaneously kill target cells without any prior immunization or stimulation. NK cells exert then tumoricidal process through the release of granules that contain granzyme B, a serine protease. Granzyme B is constitutively expressed in NK cells and can be up-regulated by cytokines including IL-12 and IL-2; consequently, their cytotoxicity can be enhanced by stimulation with these cytokines. FIG. 3 showed that the level of GZMB gene expression was higher with IL-12 or IL-2 plus lunasin compared to cytokine alone. FIG. 11 further showed that cytokine IL-2 or IL-12 plus lunasin results in increased granzyme B (GZMB) gene expression by human primary NK cells following stimulation over 3 days compared to cytokine or lunasin treatment alone. Freshly isolated human NK cells from peripheral blood mononuclear cells (PBMCs) of normal controls using positive selection with CD56 magnetic beads (Miltenyi Biotec, Auburn, Calif.) were stimulated with medium only (−), IL-12 (10 ng/ml), IL-12 (10 ng/ml) +lunasin (20 µM), IL-2 (100 unit/ml), IL-2 (100 unit/ml)+lunasin (20 µM) or lunasin alone (20 µM). Following 1, 2, and 3 days of stimulation, the cell pellets were lysed in Trizol Reagents for total RNA extraction. The first-strand cDNA was synthesized followed by real time qPCR using TaqMAN Assay with primer for granzyme B (GZMB) in ABI 7300. Results are presented as mean±SD from duplicates.

Lunasin Augments Cytotoxicity by Cytokine-Activated NK Cells

Figure 12:
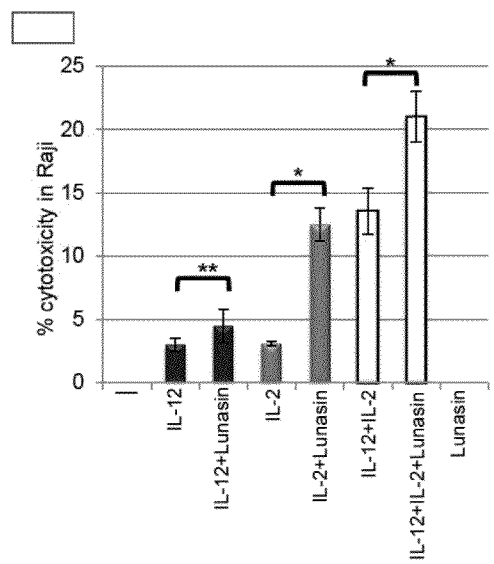
FIG. 12 NK cell-mediated cytotoxicity in a human B-lymphoma cell line (Raji). Freshly isolated NK cells (described in FIG. 3) were stimulated with medium only (−), IL-12 (1 ng/ml or IL-2 (10 units/ml) only, lunasin only (50 μM), IL-12 or IL-2 +lunasin, or IL-12 and IL-2 +lunasin as indicated for 1 day. The target cell Raji (a human B-lymphoma cell line) was provided by Dr. Shivani Srivastava, The in vitro cytotoxicity assay was measured using lactase dehydrogenase (LDH)-releasing assay with the CytoTox 96 non-Radioactive Cytotoxicity Assay Kit (Promega, Madison WI). The effector were co-cultured with target cells at ratio of 10:1 for 4 hrs at 37 C in a 5% $CO_2$ incubator. The % of cytotoxicity was calculated according to the manufacturer's instructions. Data are presented as mean±SD from 2 duplicates, Results shown are representative from 3 independent experiments, *P<0.05; **P>0.05.

Our results showed that lunasin acted synergistically with IL-12 or IL-2 to activate NK cells that had higher levels of IFNγ production. To determine whether activated NK cells have augmented cytotoxicity following stimulation with lunasin, we measured their killing activity using the In Vitro Cytotoxicity Assay. As expected, cytokine-activated NK cells exhibited higher cytolytic activity against Raji lymphoma cells as compared to that with unstimulated effectors (FIG. 12). Moreover, NK cells stimulated with the combination of lunasin and single cytokine or both cytokines mediated cytotoxicity superior to that by NK cells activated with single or both cytokines alone (FIG. 12). These in vitro results have demonstrated the ability of lunasin synergistically works with single or both cytokines IL-12 and IL-2 to enhance the tumoricidal activity of NK cells against Raji lymphoma cells that are resistant to NK-mediated killing.

FIG. 12 shows NK cell-mediated cytotoxicity in a human B-lymphoma cell line (Raji).

Freshly isolated NK cells (described in FIG. 3) were stimulated with medium only (−), IL-12 (1 ng/ml) or IL-2 (10 units/ml) only, lunasin only (50 µM), IL-12 or IL-2+lunasin, or IL-12 and IL-2 +lunasin as indicated for 1 day. The target cell Raji (a human B-lymphoma cell line) was provided by Dr. Shivani Srivastava. The in vitro cytotoxicity assay was measured using lactase dehydrogenase (LDH)-releasing assay with the CytoTox 96 non-Radioactive Cytotoxicity Assay Kit (Promega, Madison, Wis.). The effectors were co-cultured with target cells at ratio of 10:1 for 4 hrs at 37 C in a 5% $CO_2$ incubator. The % of cytotoxicity was calculated according to the manufacturer's instructions. Data are presented as mean±SD from 2 duplicates. Results shown are representative from 3 independent experiments. *$P<0.05$; **$P>0.05$.

Figure 13:
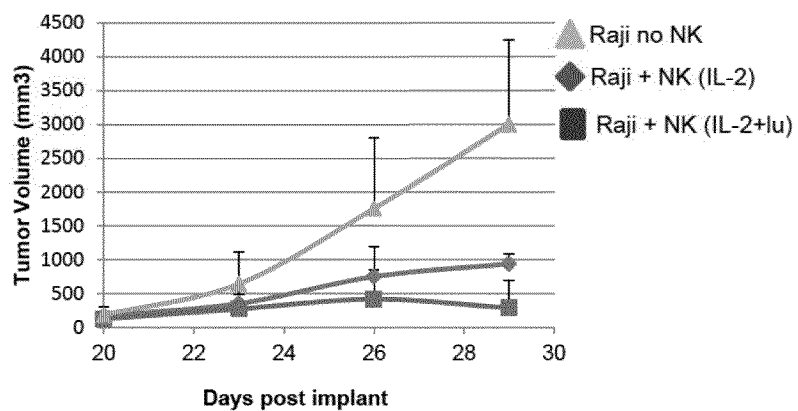
FIG. 13 Lunasin augments cytotoxicity by cytokine-activated NK cells in a xenograft model of human B-lymphoma. Immune deficient NOD/SCID/gc$^{null}$ (NSG) mice were injected subcutaneously on day 1 with 0.1 million Raji cells in 0.1 ml PBS mixed with 0.1 ml Matrigel(BD Siosciences, San Jose, CA). On day 2, these mice were injected subcutaneously with PBS only (no NK) or 0.5 million NK cells stimulated overnight with IL-2 or IL-2 plus lunasin. Tumor size was measured daily with calipers for 3 weeks, and the tumor volume was calculated. Data are presented as mean±SD from 2-3 mice in each group.

Lunasin Augments Cytotoxicity by Cytokine-Activated NK Cells in a Xenograft Model of Human B-Lymphoma Cellular therapy using NK cells activated in vitro has been tested clinically against several tumors, including hematologic malignancies and solid tumors such as melanoma, renal cell carcinoma, breast cancer, ovarian cancer and neuroblastoma. Our in vitro cytotoxicity assay supports that activated NK cells using lunasin and cytokine(s) are superior to those activated with cytokine(s) alone (FIG. 12), which may provide a more efficacious NK-based cellular therapy in vivo. We next evaluated the in vivo cytolytic activity of activated NK cells in human Raji lymphoma xenograft model. As expected, tumor growth has increased over time in the control group without transferred NK cells. While tumor growth has attenuated in mice receiving NK cells activated with cytokine, the group receiving NK cells activated with lunasin and cytokine had lowest tumor size when compared to the group receiving NK cells activated with cytokine only (FIG. 13).

These results support that the combination of IL-12 or IL-2 with lunasin is superior to cytokine alone for enhancing NK cell tumoricidal activity.

Increased Expression of NCR2 in NK Cells Accompanies Elimination of Tumor Cells

The cytotoxicity of NK cells is also regulated by the net signaling events triggered by invariant activating and inhibitory receptors that recognize the ligands on target cells. Many of the killer-cell immunoglobulin-like receptors (KIR) on NK cells recognize MHC class I ligands on target cells, which inhibit NK cell-mediated cytotoxicity. The activating receptors involved in NK-mediated cytolysis are NKG2D and the natural cytotoxicity receptors (NCRs) including NCR1 (NKp46 or CD335), NCR2 (NKp44 or CD336), and NCR3 (NKp30 or CD337). It has been shown that the tumor-killing activity of NK cells is correlated with the levels of NCR expression (see FIG. 14), and NCR2 is involved in NK-mediated cytotoxicity against lung adenocarcinoma A549.

Figure 14:
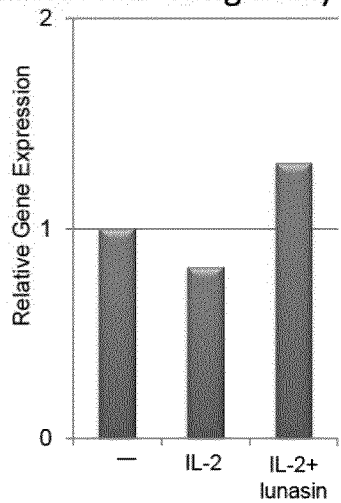
FIG. 14a. NCR2 gene expression (NCR2) by human primary NK cells following 1 day of stimulation. Freshly isolated human NK cells from peripheral blood mononuclear cells (PBMCs)of normal control(DH54)using positive selection with CD56 magnetic beads (Miltenyi Biotec, Auburn, CA) were stimulated with medium only (−), IL-2 (100 unit/ml) or IL-2 (100 unit/ml)+lunasin (40 mM). Following 1 day of stimulation, the cell pellets were lysed in Trizol Reagents for total RNA extraction. The first strand cDNA was synthesized followed by real time qPCR using Taqman Assay with primer for natural cytotoxicity receptor 2 (NCR2) in ABI 7300.
FIG. 14b. NCR2 gene expression (NCR2) by human primary NK cells following 3days of stimulation. Freshly isolated human NK cells from peripheral blood mononuclear cells (PBMCs) of normal controls using positive selection with CD56 magnetic beads (Miltenyi Biotec, Auburn, CA) were stimulated with medium only (−), IL-2(10 ng/ml) or IL-12 (10 ng/ml)+lunasin (20 mM). Following 3 days of stimulation the cell pellets were lysed in Trizol Reagents for total RNA extraction. The first-strand cDNA was synthesized followed by real time qPCR using Taqman Assay with primer for natural cytotoxicity receptor 2(NCR2) in ABI 7300. Results are presented as mean±SD from duplicates.
Figure 14:
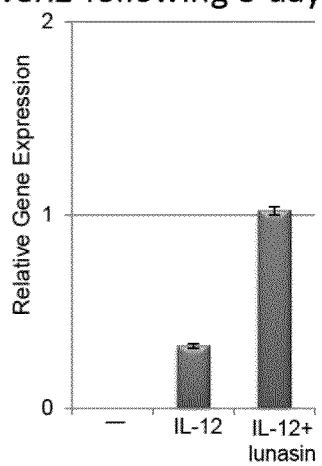

FIG. 14 showed that NK cells heated with IL-12 or IL-2 plus lunasin had increase of NCR2 expression as compared to those treated with medium, or cytokine only after incubation. At day 3, NCR2 expression was undetectable in NK cells treated with medium only while it was 5 fold higher in cells with IL-12 and lunasin than those with IL-12 alone (FIG. 14b). Similar results were observed for IL-2 treatment in combination of lunasin (see FIG. 14a, IL-2 panels). These results suggest that the combination of cytokine IL-12 or IL-2 with lunasin is capable of regulating expression of receptors that modulate NK-mediated cytotoxic effects.

Reduced Expression of KIRs in NK Cells Accompanies Elimination of Tumor Cells

Figure 15:
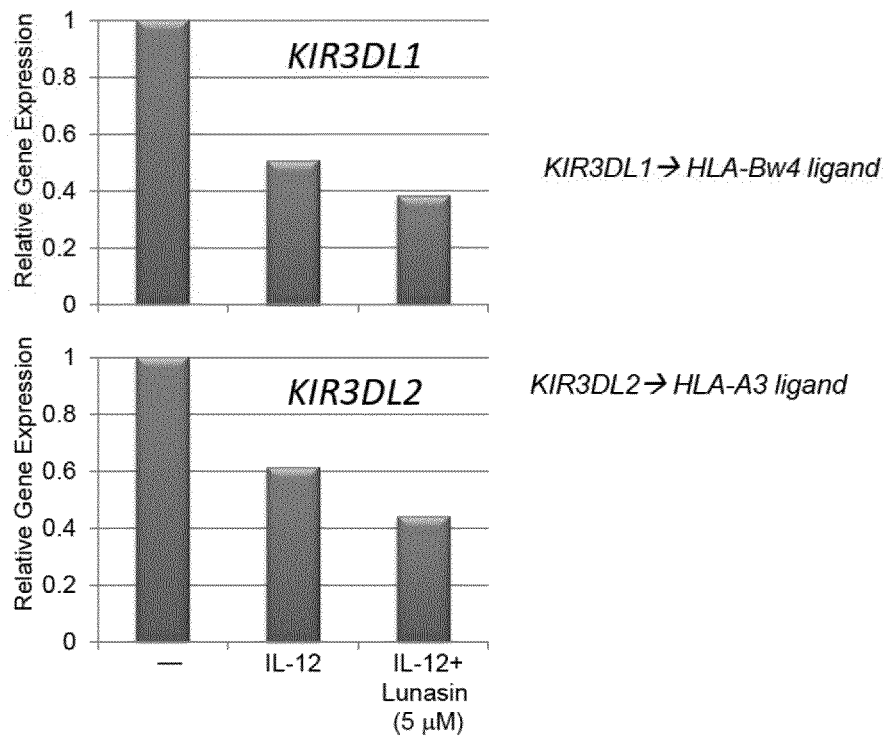
FIG. 15 KIR3DL1 and KIR3DL2 gene expression levels of human NK cells following stimulation. Freshly isolated human NK cells from peripheral blood mononuclear cells (PBMCs) of normal control using positive selection with CD56 magnetic beads (Miltenyi Biotec Auburn CA) were stimulated with medium only (−), IL-12 (10 ng/ml) or IL-12 (10ng/m1)+lunasin (5 mM) for 1 day. The cell pellets were lysed in Trizol Reagents for total RNA extraction. The first-strand cDNA was synthesized followed by real time qPCR using Tagman Assay with primer for inhibitory receptors KIR3DL1 (upper panel) and KIR3DL2(lower panel) in ABI 7300.

FIG. 15 shows KIR3DL1 and KIR3DL2 gene expression levels of human NK cells following stimulation. Freshly isolated human NK cells from peripheral blood mononuclear cells (PBMCs) of normal control using positive selection with CD56 magnetic beads (Miltenyi Biotec, Auburn, Calif.) were stimulated with medium only (−), IL-12 (10 ng/ml) or IL-12 (10 ng/ml)+lunasin (5 µM) for 1 day. The cell pellets were lysed in Trizol Reagents for total RNA extraction. The first-strand cDNA was synthesized followed by real time qPCR using Taqman Assay with primer for inhibitory receptors KIR3DL1 (upper panel) and KIR3DL2 (lower panel) in ABI 7300. The reduced KIRs expression in the presence of lunasin indicates lunasin facilitates the down regulation of inhibitory receptors on NK cells, therefore activating NK's tumoricidal activity.

Figure 16:
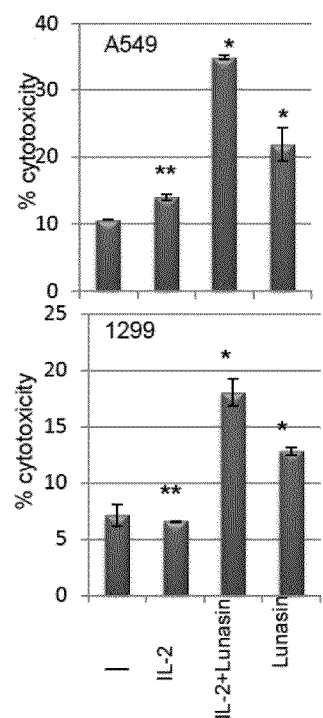
FIG. 16 NK cell mediated cytotoxicity in lung cancer cell lines. Freshly isolated NK cells (described in FIG. 1) were stimulated with medium only (−) IL-2 (10 units/ml). IL-2(10 units/ml)+lunasin (50 μM) for 1 day The target cell lung cancer cell line A549 (upper panel) and 1299(lower panel) was provided by Dr. Martin Smith at IUSM. The in vitro cytotoxicity assay was measured using lactase dehydrogenase (LDH)-releasing assay with the CytoTox 96 non-Radioactive Cytotoxicity Assay Kit (Promega, Madison, WI). The effector were co-cultured with target cells at ratio of 5:1 for 4 hrs at 37 C in a 5% $CO_2$ incubator. The % of cytotoxicity was calculated according to the manufacturer's instructions. Data are presented as mean±SD from duplicates. Results shown are representative from 2independent experiments. *P<0.05 and **P>0.05, relative to NK stimulated with medium only.

Our data here have suggested additional effects of lunasin on anti-tumor immunity by augmenting NK cell cytotoxicity. Indeed, our initial studies demonstrate that NK cells stimulated with IL-12 or IL-2 plus lunasin resulted in a higher cytotoxicity against not only hematopoietic malignants (human B-lymphoma cell line Raji in FIG. 12) but also solid tumors (human lung cancer cell lines A549 and 1299 in FIG. 16) compared to medium alone. The study reveals the tumoricidal activity of NK cells is correlated with the expression levels of granzyme B and/or NCR2, and reversely correlated with the expression level of inhibitory KIRs.

Figure 17:
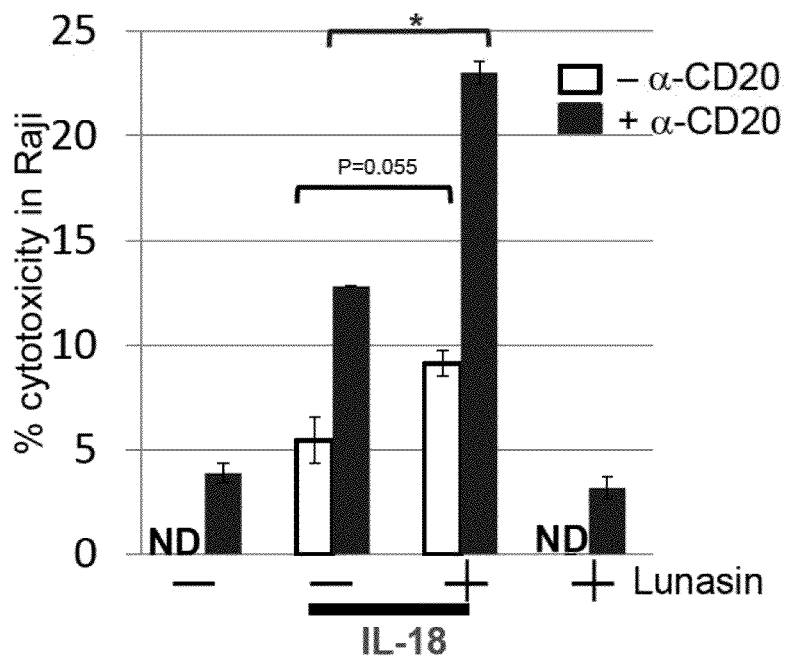
FIG. 17 Lunasin enhances IL-18-stimulated ADCC by human NK cells. Freshly isolated human NK cells as described in FIG. 1 were stimulated overnight in medium only (−), IL-18 (100 ng/ml) in the absence (−)or presence (+)of lunasin peptide. The target Raji cells were pre-treated or not with rituximab (anti-CD20 mAb at 0.1 ug/ml)for 2 hrs followed by the 4-hr in vitro cytotoxicity assay the CytoTox 96 non-Radioactive Cytotoxicity Assay Kit (Progega, Madison, WI). The % of cytotoxicity was calculated according to the manufacturer's instructions. Data are presented as mean±SD from duplicates. *P<0.05; ND, not detectable.

Results from our study suggest that allogeneic NK cells can be manipulated to reduce their expression of inhibitory receptors using lunasin peptides, which can mediate potent graft-versus-leukemia (GVL) effects after adoptive transfer.
Lunasin Enhances IL-18-stimulated Antibody-Dependent Cellular Cytotoxicity (ADCC) Activity by NK Cells FIG. 17 shows Lunasin enhances IL-18-stimulated ADCC by human NK cells. Briefly, freshly isolated human NK cells as described in FIG. 1 were stimulated overnight in medium only (−). IL-18 (100 ng/ml) in the absence (−) or presence (+) of lunasin peptide. The target Raji cells were pre-treated or not with rituximab (anti-CD20 mAb at 0.1 ug/ml) for 2 hrs followed by the 4-hr in vitro cytotoxicity assay the CytoTox 96 non-Radioactive Cytotoxicity Assay Kit (Promega, Madison, Wis.). The % of cytotoxicity was calculated according to the manufacturer's instructions. Data are presented as mean±SD from duplicates. *P<0.05; ND, not detectable.

Example 4

Effects of Lunasin on Dendritic Cells (DCs) and Macrophages (FIGS. 18-23)

In this example we showed that lunasin in combination with other cytokines promotes robust IFNγ production in various dendritic cells and macrophages. Similar to NK cells, dendritic cells and macrophages are involved in innate immune responses with multiple functions including secreting various cytokines upon stimulation, or increasing co-stimulating molecule after being stimulated by an antigen. Adding lunasin into the treatment regimen synergistically enhance the effects imposed by the selective cytokines on these innate immune cell types.

Figure 18:
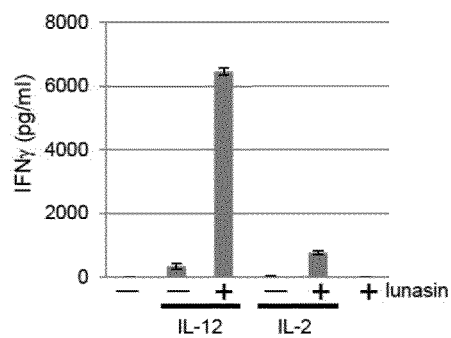
FIG. 18 The levels of IFNγ production by human plasmacytoid dendritic cells (pDCs) from normal controls following stimulation. Freshly isolated human pDC cells from peripheral blood mononuclear cells (PBMCs) of normal controls using the CD304 (BDCA-4/Neuropilin-1 ) microbeads (Millenyi Biotec, Auburn, CA) were stimulated with medium only(−), IL-12(10 ng/ml), IL-12(10 ng/ml)+lunasin(50 mM), IL-2 (100 unit/ml), IL-2 (100unit/ml)+lunasin (50 mM) or lunasin alone(50 mM). One day following stimulation, the supernatants were collected for measuring the production of IFNg using ELISA. Data are presented as mean±SD from duplicates. Results shown are representative from over 3different normal controls.

FIG. 18 shows levels of IFNγ production by human plasmacytoid dendritic cells (pDCs) from normal controls following stimulation. Freshly isolated human pDC cells from peripheral blood mononuclear cells (PBMCs) of normal controls using the CD304 (BDCA-4/Neuropilin-1) microbeads (Miltenyi Biotec, Auburn, Calif.) were stimulated with medium only (−), IL-12 (10 ng/ml), IL-12 (10 ng/ml)+lunasin (50 mM), IL-2 (100 unit/ml), IL-2 (100 unit/ml)+lunasin (50mM) or lunasin alone (50 mM). One day following stimulation, the supernatants were collected for measuring the production of IFNg using ELISA. Data are presented as mean±SD from duplicates. Results shown are representative from over 3 different normal controls.

Figure 19:
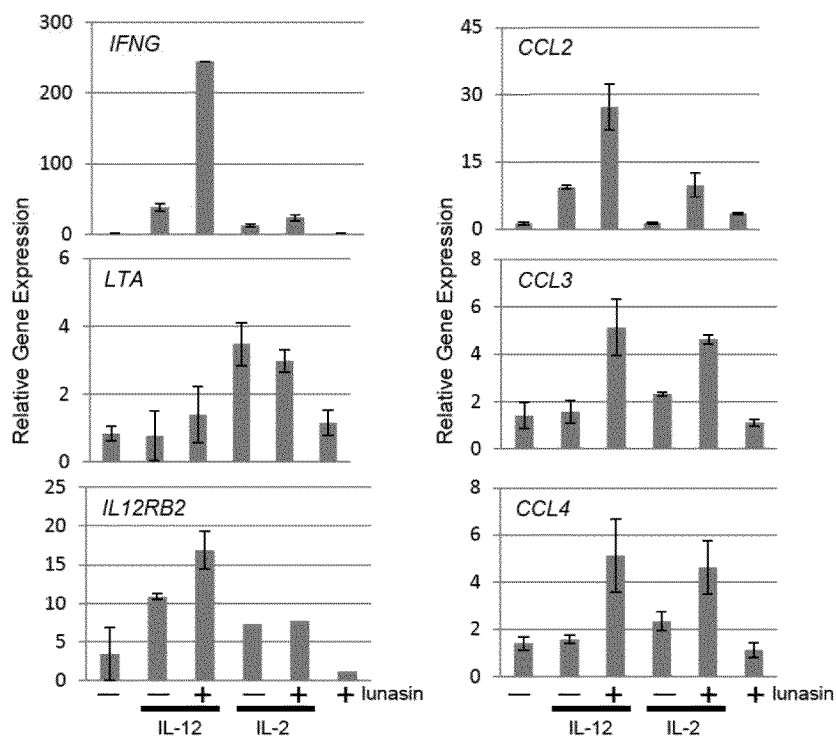
FIG. 19 Effects of lunasin on gene expression by human pDC. Freshly isolated human pDC cells from peripheral blood nononuclear cells (PBMCs) of normal controls using the CD304 (BDCA-4/Neuropilin-1) microbeads (Miltenyi Biotec, Auburn CA) were stimulated as described in the FIG. 16. One day following stimulation the cell pellets were resuspended in Trizol Reagents for total RNA extraction The first-strand cDNA was synthesized followed by real time qPCR using Taqman Assay with primers for gene expression using the ABI 7300(Applied Biosystems by Life Technologies, Carlsbad, CA). Data are presented as mean±SD from duplicates. Results shown are representative from over 3 different normal controls.

FIG. 19 shows Effects of lunasin on gene expression by human pDC. Freshly isolated human pDC cells from peripheral blood mononuclear cells (PBMCs) of normal controls using the CD304 (BDCA-4/Neuropilin-1) microbeads (Miltenyi Biotec, Auburn, Calif.) were stimulated as described in the FIG. 18. One day following stimulation, the cell pellets were resuspended in Trizol Reagents for total RNA extraction. The first-strand cDNA was synthesized followed by real time qPCR using Taqman Assay with primers for gene expression using the ABI 7300 (Applied Biosystems by Life Technologies, Carlsbad, Calif.). Data are presented as mean±SD from duplicates. Results shown are representative from over 3 different normal controls.

Figure 20:
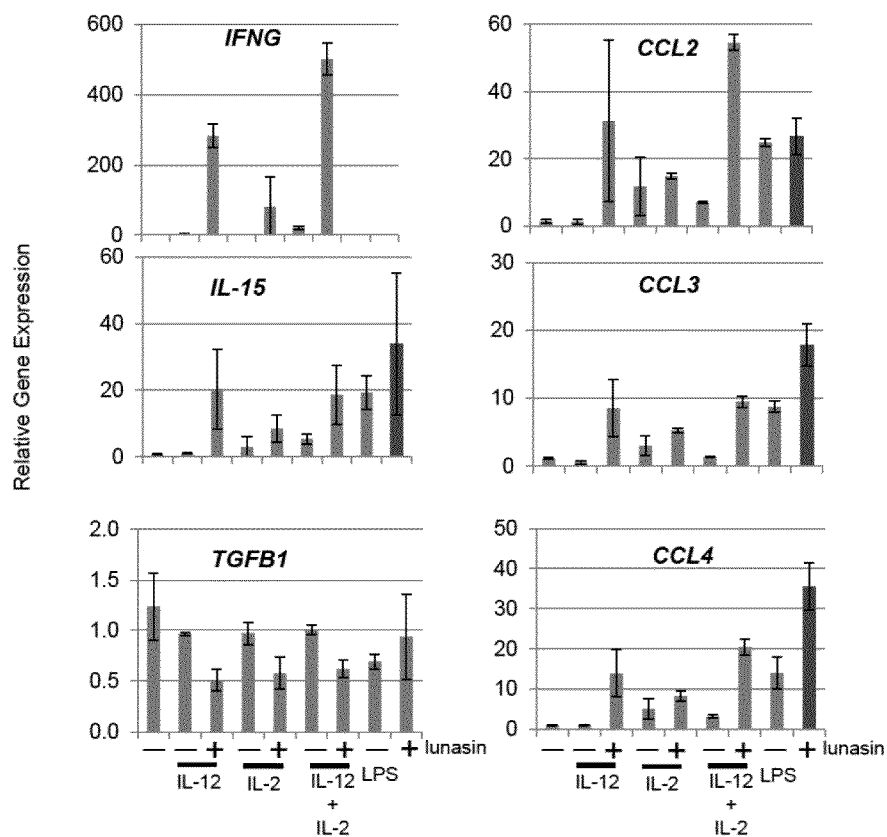
FIG. 20 Effects of lunasin on gene expression by human cDC, Freshly isolated human cDC cells from peripheral blood mononuclear cells (PBMCs) of normal controls using CD1c (BDCA-1) microbeads (Miltenyi Biotec, Auburn, CA) were stimulated as indicated. One day following stimulation, the cell pellets were resuspended in Trizol Reagents for total RNA extraction. The first-strand cDNA was synthesized followed by real time qPCR using Taqman Assay with primers for gene expression using the ABI 7300 (Applied Biosystems by Life Technologies, Carlsbad, CA). Data are presented as mean±SD from duplicates. Results shown are representative from over 3 different normal controls.

FIG. 20 shows Effects of lunasin on gene expression by human cDC. Freshly isolated human cDC cells from peripheral blood mononuclear cells (PBMCs) of normal controls using the CD1c (BDCA-1) microbeads (Miltenyi Biotec, Auburn, Calif.) were stimulated as indicated. One day following stimulation, the cell pellets were resuspended in Trizol Reagents for total RNA extraction. The first-strand cDNA was synthesized followed by real time qPCR using Taqman Assay with primers for gene expression using the ABI 7300 (Applied Biosystems by Life Technologies, Carlsbad, Calif.). Data are presented as mean±SD from duplicates. Results shown are representative from over 3 different normal controls.

Figure 21:
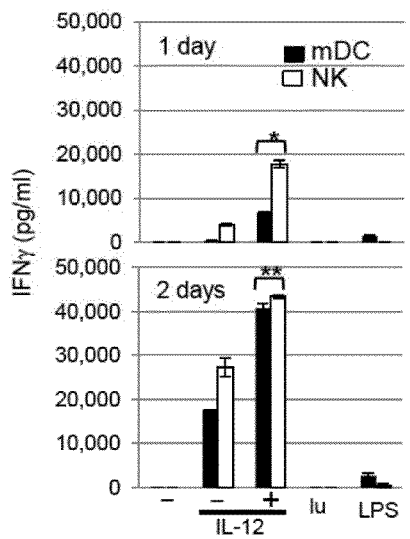
FIG. 21 Effects of lunasin on IFNγ production by myeloid dendritic cells (mDCs) and NK cells from mice. Freshly isolated mDCs from spleens of C57BL6 mice using the CD11c microbeads (Miltenyi Biotec, Auburn, CA) were stimulated with medium (−), mIL-12(2 ng/ml without(−) or with (+) lunasin, lunasin (lu, 50 mM) or lipopolysaccharide (LPS) (1 μg/ml) alone for 1 and 2 days. NK cells isolated from the same mice using DX5 microbeads were stimulated with the same conditions indicated. The levels of IFNγ in the supernatants were determined using ELISA. Data are presented as mean ±SD from duplicates. Results shown are representative from 2 mice. *P<0.05; **P>0.05.

FIG. 21 shows Effects of lunasin on IFNγ production by myeloid dendritic cells (mDCs) and NK cells from mice. Freshly isolated mDCs from spleens of C57BL6 mice using the CD11c microbeads (Miltenyi Biotec, Auburn, Calif.) were stimulated with medium (−), mIL-12 (2 ng/ml) without (−) or with (+) lunasin, lunasin (lu, 50 mM) or lipopolysaccharide (LPS) (1 μg/ml) alone for 1 and 2 days. NK cells isolated from the same mice using DX5 microbeads were stimulated with the same conditions indicated. The levels of IFNγ in the supernatants were determined using ELISA. Data are presented as mean±SD from duplicates. Results shown are representative from 2 mice. *P<0.05; **P>0.05

Figure 22:
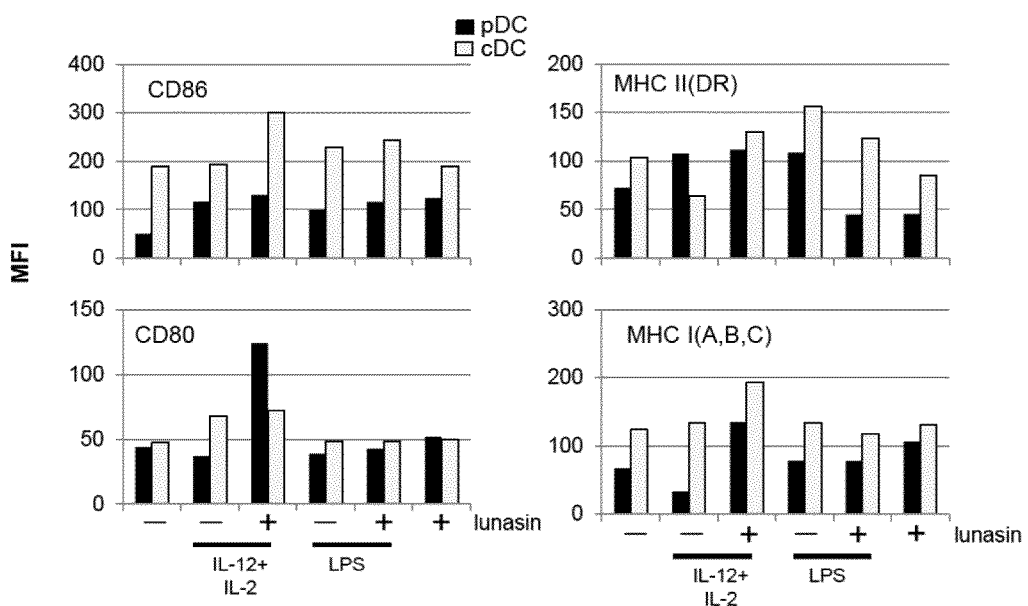
FIG. 22 Effects of lunasin on levels of surface molecules DCs. Freshly isolated human pDC and cDC cells from peripheral blood mononuclear cells (PBMCs) of normal controls were stimulated as indicated One day following stimulation expression of surface molecules, including major histocompatibility complex (MHC) class I and class II, as well as co-stimulatory molecules CD80 and CD86, was analyzed using flow cytometrv with commercial available antibodies. The levels of surface molecules were evaluated on 5000events and presented as mean fluorescent intensity (MFI).

FIG. 22 shows Effects of lunasin on levels of surface molecules on DCs. Freshly isolated human pDC and cDC cells from peripheral blood mononuclear cells (PBMCs) of normal controls were stimulated as indicated. One day following stimulation, the expression of surface molecules, including major histocompatibility complex (MHC) class I and class II, as well as co-stimulatory molecules CD80 and CD86, was analyzed using flow cytometry with commercial available antibodies. The levels of surface molecules were evaluated on 5000 events and presented as mean fluorescent intensity (MFI).

Figure 23:
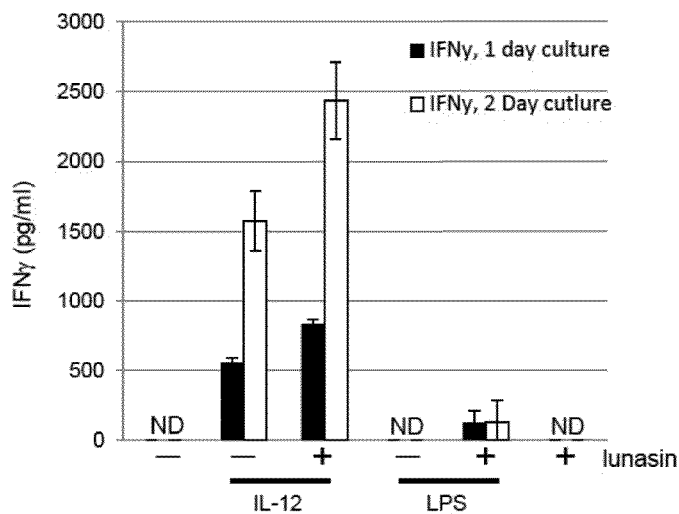
FIG. 23 Effects of lunasin on IFNγ production by macrophages from mice. Freshly isolated macrophages from spleens of C57BL6 mice using the CD11b microbeads (Miltenyi Biotec Auburn, CA) were stimulated as indicated for 1 and 2 days. The levels of IFNγ in the supernatants were determined using ELISA. Data are presented as mean ±SD from duplicates.

FIG. 23 shows Effects of lunasin on IFNγ production by macrophages from mice. Freshly isolated macrophages from spleens of C57BL6 mice using the CD11b microbeads (Miltenyi Biotec, Auburn, Calif.) were stimulated as indicated for 1 and 2 days. The levels of IFNγ in the supernatants were determined using ELISA. Data are presented as mean±SD from duplicates.

Example 5

Effect of Lunasin on Modulating Allergic Inflammation

There is a plethora of evidence that Th2-mediated inflammation can promote allergic disease when IFNγ production is reduced to free from its restraining influence. It has been shown that development of spontaneous airway inflammation consistent with human asthma was found in mice lacking a transcription factor T-bet, a master regulator of Th1 development and IFNγ production. These results suggest that upregulating Th1 cytokine IFNγ is a potential strategy to reduce the risk of asthma and allergic disease.

Our studies found that soy peptide lunasin alone or in combination with IL-12 or IL-2 had effects on enhancing the production of IFNγ by human and mouse NK cells. In addition, dietary supplementation of gavaged lunasin maintains its bioactivity, which can be found in the lung and blood. Taken together, these results suggest the ability of lunasin to induce IFNγ production by NK cells and therefore, may suppress Th2-mediated allergic inflammation.

Figure 24:
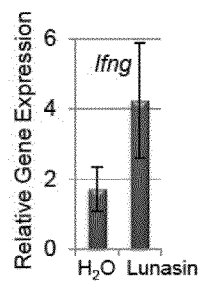
FIG 24 Gene expression of Ifng from mice treated with lunasin. Balb/c mice were gavaged with 200 ml of water only ($H_2O$) or 4 mg of lunasin in 200 ml water (Lunasin) for 3 consecutive days. One day after the last gavage. mice were sacrificed to collect the lungs. NK cells were isolated from lungs of each mouse using positive selection with DX5 magnetic beads (Miltenyi Biotec) followed by RNA extraction, cDNA synthesis and real time qPCR using Taqman assay primers (ABI). Gene expression for IFNg (Ifng) from lungs is presented as mean±SD from 2 mice in each group.

FIG. 24 shows increased gene expression of Ifng in the lung from mice treated with lunasin. Balb/c mice were gavaged with 200 μl of water only ($H_2O$) or 4 mg of lunasin in 200 μl water (Lunasin) for 3 consecutive days. One day after the last gavage, mice were sacrificed to collect the lungs and spleens. NK cells were isolated from each lung and spleen using positive selection with DX5 magnetic beads (Miltenyi Biotec) followed by RNA extraction, cDNA synthesis and real tune qPCR using Taqman assay primers (ABE). Gene expression for Ifng from lungs (upper panel) and spleens (lower pannel) is presented as mean±SD from 2 mice in each group.

This study supported in vivo stimulatory effects of lunasin on NK cells for increasing the production of IFNγ, which may suppress Th2-mediated allergic inflammation.

Figure 25:
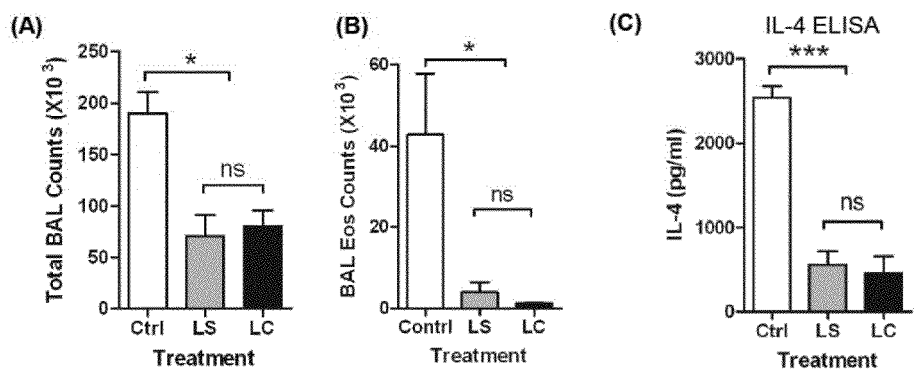
FIG. 25 Lunasin-treated mice have reduced allergic inflammation in a mouse model of asthma. In LPS-induced asthma model BABL/c mice were sensitized intranasally with 0.1 μg of LPS at day 0, 1, and 2 with (LS) or without (Ctrl) lunasin peptide at 4 mg, and then challenged with 50 μg of OVA on days 19, 20 and 21. Another group of mice (LC) was sensitized as the Ctrl group followed by challenging with OVA in the presence of lunasin at 4mg. The total cell numbers (A) and differential cell numbers of eosinophils (B) were counted from the BAL fluid. Data are presented as mean±SD from 3 mice in each group. *, P<0.05; ns not-significant p>0.05. (C) Cells from draining lympho nodes (mediastinal) were stimulated with OVA, and the levels of IL-4 production in the supernatants were evaluated using ELISA. Data are presented as mean ±SD from 3 mice in each group. ***, P<0.005; ns, not-significant, p>0.05.

In this example we showed Lunasin-treated mice have reduced allergic inflammation evidenced by lower cell counts in the bronchoalveolar lavage (BAL) fluid, and reduced production of IL-4 in the LPS-induced asthma mouse model Briefly, FIG. 25 shows cell counts in the bronchoalveolar lavage (BAL) fluid and IL-4 production in a mouse model of asthma. In LPS-induced asthma model, BABL/c mice were sensitized intranasally with 0.1 μg of LPS at day 0, 1, and 2 with (LS) or without (Ctrl) lunasin peptide at 4 mg, and then challenged with 50 ug of OVA on days 19, 20, and 21. Another group of mice (LC) was sensitized as the Ctrl group followed by challenging with OVA in the presence of lunasin at 4 mg. The total cell numbers (A) and differential cell numbers of eosinophils (B) were counted from the BAL fluid. Data are presented as mean±SD from 3 mice in each group. *, $P<0.05$; ns (not-significant), $p>0.05$. (C) Cells from draining lympho nodes (mediastinal) were stimulated with OVA, and the levels of IL-4 production in the supernatants were evaluated using ELISA. Data are presented as mean±SD from 3 mice in each group. ***, $P<0.05$: ns (not-significant), $p>0.05$. (Chi: low LPS sensitization, OVA challenge; LS: Low LPS sensitization with lunasin, OVA challenge; LC: Low LPS sensitization, OVA challenge with lunasin)

Example 6

The Effects of Lunasin on Therapeutic Prevention for Cancer in Mouse Models

Therapeutic vaccines are designed to stimulate anti-tumor immune responses against various malignances, which could be potentially used as a treatment regimen for cancer patients. In addition, combining a cancer vaccine with an immune activating agent such as cytokine can further enhance the clinical outcomes that improve progression-free survival in patients.

There are superior anti-tumor responses using a chimeric HER2 peptide vaccine that is composed of HER2 B-cell epitope fused to a promiscuous T-cell epitope from measles virus fusion protein (MAT7). A more recent phase I study using these therapeutic peptide vaccines showed clinical activity in patients with metastatic and/or recurrent solid tumors. Combining IL-12 with two peptide vaccines (MVF $HER2_{316-339}$ and MVF $HER2_{628-647}$) resulted in significant reduction on the development of pulmonary metastases in a syngeneic HER2/neu tumor model. Without limiting the theories, one explanation for conferring protection in this model has been attributed to increased production of IFNγ following IL-12 treatment, which promotes the isotype switch to IgG2a that mediates ADCC activity in mice treated with these peptide vaccines.

In our studies, the combination of lunasin with IL-12 is superior to IL-12 alone for induction of IFNγ by NK cells. We also observed increased expression of TNFα, GM-CSF and CCL3 (macrophage inflammatory protein-1α or MIP-1α) which may facilitate the development of inflammatory environment by recruiting more immune cells and promotes the differentiation of dendritic cells from monocytes. In addition, our new data in both human and murine systems demonstrated that cDCs produced IFNγ and up-regulated the surface levels of co-stimulatory molecules (e.g., CD80 and CD86) as well as MHC class II following stimulation with lunasin and IL-12. These results suggest that lunasin may enhance the adjuvanticity of IL-12 in vivo.

We want to test the hypothesis that lunasin and IL-12 will enhance the anti-tumor effects mediated by the peptide vaccine (MVF $HER2_{316-339}$ and MVF $HER2_{628-647}$), and therefore a more efficacious therapeutic vaccine against HER2 positive tumors. The effectiveness of lunasin and IL-12 in therapeutic vaccine will be evaluated in a syngeneic HER2/neu tumor model as established.

Tumor volume will be measured daily with calipers as described. One week after the last vaccination, immune responses will be measured. Sera collected will be evaluated for the levels of IFNγ and antibody isotype using ELISA. Intracellular cytokine staining from splenocytes will be performed to determine if NK, cDC and/or macrophage populations are responsible for IFNγ production. The tumoricidal activity of NK cells from these mice will be measured against the target cell line CT-$26^{HER/neu}$ as described. Statistic consideration is followed as previously described.

Control group of mice receiving PBS will have the largest tumor volume at the end of the study. Results will demonstrate an improved adjuvanticity of lunasin and IL-12 in enhancing the anti-tumor immunity for HER2 peptide vaccines as therapeutic treatment. As a result, these mice will suppress tumor growth and have reduced tumor volume.

The invention claimed is:

1. A combination therapy of lunasin and at least one cytokine selected from the group consisting of, interleukin 15 (IL-15) interleukin 18(IL-18), and interleukin 21 (IL21), wherein the combination therapy enhances the at least one cytokine's effect on an innate immune system.

2. The combination therapy of claim 1, wherein the combination therapy enhances innate immune system expression of Interferon-γ(IFN-γ), IL-15, chemokine(c-c motif) lignad 2(CCL2), chemokine(c-c motif)ligand 3(CCL3), chemokine (c-c motif) ligand 4(CCL4) or Granulocyte-macrophage colony-stimulating factor (GM-CSF).

3. The combination therapy of claim 1, wherein the combination therapy attenuates suppression of Th1 switch.

4. The combination therapy of claim 1, wherein the combination therapy enhances natural killer NK cell cytotoxicity by increasing expression of Granzyme B and natural cytotoxicity triggering receptor 2 (NCR2).

5. The combination therapy of claim 1, wherein the combination therapy enhances NK cell cytotoxicity by decreasing expression of inhibitory killer-cell immunoglobulin-like receptors (KIR).

6. The combination therapy of claim 1, wherein the combination therapy enhances antibody-dependent cell mediated cytotoxicity (ADCC) by NK cells.

7. A method of enhancing an innate immune system, the method comprising providing an individual with a pharmaceutically effective amount of a combination of lunasin and at least one cytokine selected from the group consisting of IL-15, IL-18, and IL-21.

8. The method of claim 7, wherein the enhanced immune system has natural killer (NK) cells with increased expression of natural cytotoxicity triggering receptor 2(NCR2) and Granzyme B.

9. The method of claim 7, wherein the enhanced immune system has NK cells with decreased expression of killer-cell immunoglobulin receptors (KIR).

10. The method of claim 7, wherein the enhanced immune system has NK cells with increased antibody dependent cell mediated cytotoxicity (ADCC).

11. A method of enhancing activity of natural killer (NK) cells, the method comprising providing an individual with a pharmaceutically effective amount of a combination of lunasin and at least one cytokine selected from the group consisting of IL-15, IL-18, and IL-21.

12. A method of increasing antibody dependent cell mediated cytotoxicity (ADCC) by natural killer (NK) cells, the method comprising providing an individual with a pharmaceutically effective amount of a combination of lunasin and at least one cytokine selected from the group consisting of IL-15, IL-18, and IL-21.

13. The method of claim 11, wherein the NK cells have increased expression of Granzyme B or natural cytotoxicity triggering receptor 2 (NCR2).

* * * * *